United States Patent
Zdrojkowski et al.

(10) Patent No.: US 6,305,374 B1
(45) Date of Patent: *Oct. 23, 2001

(54) BREATHING GAS DELIVERY METHOD AND APPARATUS

(75) Inventors: Ronald J. Zdrojkowski, Pittsburgh; Mark Estes, Trafford, both of PA (US)

(73) Assignee: Respironics, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/483,538

(22) Filed: Jan. 14, 2000

Related U.S. Application Data

(63) Continuation of application No. 08/823,855, filed on Mar. 25, 1997, now Pat. No. 6,029,664, which is a continuation of application No. 08/349,634, filed on Dec. 2, 1994, now Pat. No. 5,632,269, which is a continuation-in-part of application No. 07/947,156, filed on Sep. 18, 1992, now Pat. No. 5,433,193, which is a continuation-in-part of application No. 07/411,012, filed on Sep. 22, 1989, now Pat. No. 5,148,802.

(51) Int. Cl.[7] .................................................. A61M 16/00
(52) U.S. Cl. .................................. 128/204.21; 128/204.23
(58) Field of Search ........................ 128/200.24, 202.22, 128/204.18, 204.21, 204.23

(56) References Cited

U.S. PATENT DOCUMENTS

| | | | |
|---|---|---|---|
| 3,191,596 | 6/1965 | Bird et al. | 128/204.19 |
| 3,267,935 | 8/1966 | Andreason et al. | 128/200.17 |
| 3,362,404 | 1/1968 | Beasley | 128/200.21 |
| 3,485,243 | 12/1969 | Bird et al. | 128/204.25 |
| 3,580,051 | 5/1971 | Blevins | 73/40 |
| 3,669,108 | 6/1972 | Sundblom et al. | 128/204.26 |
| 3,741,208 | 6/1973 | Jonsson et al. | 128/204.21 |
| 3,896,800 | 7/1975 | Cibulka | 128/204.26 |
| 3,961,627 | 6/1976 | Ernst et al. | 128/204.21 |
| 3,972,327 | 8/1976 | Ernst et al. | 128/204.21 |

(List continued on next page.)

FOREIGN PATENT DOCUMENTS

| | | | |
|---|---|---|---|
| 484764 | 5/1976 | (AU) . | |
| 83901/82 | 4/1982 | (AU) . | |
| 615956 | 5/1989 | (AU) . | |
| 0274996 | 7/1988 | (EP) . | |
| 402951 | 12/1990 | (EP) . | |
| 0 402 951 | * 12/1990 | (EP) | 128/204.23 |
| 606687 | 7/1994 | (EP) . | |
| 1583273 | 1/1981 | (GB) . | |
| 2054387 | 2/1981 | (GB) . | |
| 8501559 | 4/1985 | (WO) . | |
| 8905669 | 6/1989 | (WO) . | |

OTHER PUBLICATIONS

Control of Nocturnal Hypoventilation by Nasal Intermittent Positive Pressure Ventilation, Carroll & Branthwaite, Thorax 1988: 43; 349–353.

Guilleminault et al., "Central Alevolar Hypoventilation and Sleep–Treatment by Intermittent Positive–Pressure Ventilation Through Nasal Mask in an Adult," Nov. 1989.

(List continued on next page.)

*Primary Examiner*—Aaron J. Lewis
(74) *Attorney, Agent, or Firm*—Michael W. Haas

(57) ABSTRACT

An improved methodology and systems for delivery of breathing gas such as for the treatment of obstructive sleep apnea through application of alternating high and low level positive airway pressure within the airway of the patient with the high and low airway pressure being coordinated with the spontaneous respiration of the patient, and improved methods and apparatus for triggering and for leak management in such systems.

9 Claims, 10 Drawing Sheets

U.S. PATENT DOCUMENTS

| | | | |
|---|---|---|---|
| 4,031,885 | 6/1977 | Davis et al. | 600/533 |
| 4,036,221 | 7/1977 | Hillsman et al. | 128/204.23 |
| 4,050,458 | 9/1977 | Friend | 128/204.23 |
| 4,082,093 | 4/1978 | Fry et al. | 128/204.25 |
| 4,207,884 | 6/1980 | Isaacson | 128/200.24 |
| 4,323,064 | 4/1982 | Hoenig et al. | 128/204.21 |
| 4,421,113 | 12/1983 | Gedeon et al. | 128/204.23 |
| 4,457,303 | 7/1984 | Durkan | 128/204.24 |
| 4,506,666 | 3/1985 | Durkan | 128/204.23 |
| 4,519,388 | 5/1985 | Schwanbom et al. | 128/204.25 |
| 4,527,557 | 7/1985 | DeVries et al. | 128/204.23 |
| 4,535,766 | 8/1985 | Baum | 128/204.23 |
| 4,539,984 | 9/1985 | Kiszel et al. | 128/204.23 |
| 4,550,726 | 11/1985 | McEwen | 128/202.22 |
| 4,567,888 | 2/1986 | Erobert et al. | 128/204.21 |
| 4,570,631 | 2/1986 | Durkan | 128/204.23 |
| 4,584,996 | 4/1986 | Blum | 128/204.21 |
| 4,592,349 | 6/1986 | Bird | 128/204.25 |
| 4,612,928 | 9/1986 | Tiep et al. | 128/204.23 |
| 4,635,631 | 1/1987 | Izumi | 128/204.21 |
| 4,637,385 | 1/1987 | Rusz | 128/204.21 |
| 4,655,213 | 4/1987 | Rapoport et al. | 128/205.25 |
| 4,667,669 | 5/1987 | Pasternack | 128/204.23 |
| 4,686,974 | 8/1987 | Sato et al. | 128/204.23 |
| 4,686,975 | 8/1987 | Naimon et al. | 128/204.23 |
| 4,773,411 | 9/1988 | Downs | 128/204.18 |
| 4,776,333 | 10/1988 | Miyamae | 128/204.21 |
| 4,782,832 | 11/1988 | Trimble et al. | 128/207.18 |
| 4,802,485 | 2/1989 | Bowers et al. | 600/324 |
| 4,807,616 | 2/1989 | Adahan | 128/204.21 |
| 4,823,787 | 4/1989 | Adahan | 128/203.27 |
| 4,823,788 | 4/1989 | Smith et al. | 128/205.24 |
| 4,830,008 | 5/1989 | Meer | 607/42 |
| 4,877,023 | 10/1989 | Zalkin | 128/204.21 |
| 4,941,469 | 7/1990 | Adahan | 128/205.18 |
| 4,957,107 | 9/1990 | Sipin | 128/204.21 |
| 5,044,362 | 9/1991 | Younes | 128/204.21 |
| 5,065,756 | 11/1991 | Rapoport | 128/204.18 |
| 5,107,830 | 4/1992 | Younes | 128/204.18 |
| 5,134,995 | 8/1992 | Gruenke et al. | 128/204.23 |
| 5,148,802 | 9/1992 | Sanders et al. | 128/204.18 |
| 5,199,424 | 4/1993 | Sullivan et al. | 128/204.18 |
| 5,259,373 | 11/1993 | Gruenke et al. | 128/204.23 |
| 5,335,654 | 8/1994 | Rapoport | 128/204.23 |
| 5,433,193 * | 7/1995 | Sanders et al. | 128/204.18 |
| 5,438,980 | 8/1995 | Phillips | 128/204.23 |
| 5,458,137 | 10/1995 | Axe et al. | 128/204.23 |
| 5,490,502 | 2/1996 | Rapoport et al. | 128/204.23 |
| 5,522,382 | 6/1996 | Sullivan et al. | 128/204.23 |
| 5,632,269 * | 5/1997 | Zdrojkowski | 128/204.23 |
| 5,645,053 | 7/1997 | Remmers et al. | 128/204.23 |
| 5,645,054 | 7/1997 | Cotner et al. | 128/204.23 |
| 5,660,171 | 8/1997 | Kimm et al. | 128/204.23 |
| 5,704,345 | 1/1998 | Berthon-Jones | 128/204.23 |
| 5,803,065 * | 9/1998 | Zdrojkowski et al. | 128/204.18 |
| 6,029,664 * | 2/2000 | Zdrojkowski et al. | 128/204.23 |

OTHER PUBLICATIONS

Lindsay et al., "Mechanisms of Sleep Desaturation in Chronic Airflow Limitation Studied with Nasal Continuous Positive Airway Pressure (CPAP)," Sidney University, N.S.W., Australia.

Sullivan et al., "Remission of Severe Obesity–Hypoventilation Syndrome after Short Term Treatment During Sleep with Nasal Continuous Positive Airway Pessure," Am. Rev. Respir. Dis., 1983.

Sullivan et al., "Reversal of Obstructive Sleep Apnoea by Continuous Positive Airway Pressure Applied Through the Nares," The Lancet Apr. 18, 1981.

Sullivan et al., "Treatment of Obstructive Sleep Apnea with Continuous Positive Airway Pressure Applied Through the Nose," Am. Rev. Respir. Dis. Annual Meeting Abstracts, 1982.

Carroll et al., "Intermittent Positive Pressure Ventilation by Nasal Mask: Technique and Applications," Intensive Care Medicine, 1988.

Ellis et al., "Treatment of Alveolar Hypoventilation in a Six–Year–Old Girl with Intermittent Positive Pressure Ventilation Through a Nose Mask," Am. Rev. Respir. Dis., 1987.

Udwadia et al., "Nasal Ventilation to Facilitate Weaning in Patients with Chronic Respiratory Insufficiency," Dept. of Respiratory Medicine, Royal Brompton Natl. Heart & Lung Hospital, London, England.

Marino, "Intermittent Volume Cycled Mechanical Ventilation Via Nasal Mask in Patients with Respiratory Failure due to COPD," Chest, Mar. 1991.

Rapoport et al., "Reversal of the "Pickwickian Syndrome" by Long–Term Use of Nocturnal Nasal–Airway Pressure," New England Journal of Medicine, Oct. 7, 1982.

Segall, "Noninvasive Nasal Mask–Assisted Ventilation in Respiratory Failure of Duchenne Muscular Dystrophy ," Chest, Jun. 1988.

Stock et al., "Airway Pressure Release Ventilation," Critical Care Medicine, May 1987.

Cox et al., "Investigation of the Spontaneous Modes of Breathing of Different Ventilators," Intensive Care Medicine, 1988.

Bach et al., "Intermittent Positive Pressure Ventilation Via Nasal Access in the Management of Respiratory Insufficiency," Chest, 1992 (?).

Viale et al., "Added Inspiratory Work of Breathing During CPAP Ventilation: Comparison of Two Demand–Valve Devices with a Continuous Flow–System," Intensive Care Medicine, 1986.

Kacmarek, "The Role of Pressure Suppot Ventilation in Reducing Work of Breathing," Respiratory Care, Feb. 1988.

MacIntyre, "Respiratory Function During Pressure Support Ventilation," Chest, May 1986.

Ellis,"Assessment and Treatment of Nocturnal Respiratory Failure–New Advances," RPA Magazine, Autumn 1988.

Sanders et al., "Patient Compliance with Nasal CPAP Therapy for Sleep Apnea," Chest, Sep. 1986.

Sanders et al., "Prolonged Expiratory Phase in Sleep Apnea," Am. Rev. Respir. Dis. 1985.

Sanders, "Nasal CPAP Effect on Patterns of Sleep Apnea," Chest, Dec. 1984.

Sanders, "CPAP Via Nasal Mask: A Treatment for Occulsive Sleep Apnea," Chest, Jan. 1983.

Weisman et al., "Intermittent Mandatory Ventilation," Am. Rev. Respir. Dis., 1983.

Kerby et al., "Nocturnal Positive Pressure Ventilation Via Nasal Mask," Am. Rev. Respir. Dis., 1987.

Nocturnal Positive Pressure Ventilation Via Nasal Mask–letter to the editor by Sullivan & Ellis, and reply from author, Am. Rev. Respir. Dis., 1987.

Baum et al., Biphasic Positive Airway Pressure (BIPAP), Anaesthesist, 1989.

Sullivan et al., Treatment of Cardiorespiratory Disturbances During Sleep, Interdiscipl. Topics Geront. (Karger, Basel 1987), pp. 47–67.

Braun, "Nocturnal Ventilation—A New Method," St. Luke's–Roosevelt Hospital, Publication Unknown.

Nursing Photobook–Providing Respiratory Care, pp. 122–126, Nursing 83 Books, Springhouse Corp., Springhouse, PA.

Sanders et al., "The Effects of Nasal CPAP on Various Sleep Apnea Patterns," Chest, 1983, Abstracts, 49th Annual Meeting of the American College of Chest Physicians.

Spearman, et al., "The New Generation of Mechanical Ventilators," Respiratory Care, Jun. 1987.

Black et al., "A Hazard of Pressure Support Ventilation," Chest, Feb. 1988.

Effects on the Work of Breathing: Flow Triggering Versus Pressure Triggering, Puritan Bennett International, Inc., Form AA 1144 (Jan. 1987).

Mahadevia et al., "Effects of Expiratory Positive Airway Pressure on Sleep–Induced Respiratory Abnormalities in Patients with Hypersomnia–Sleep Apnea Syndrome," Am. Rev. Respir. Dis., 1983.

7200a Option #50 Flow–by, Puritan–Bennett International, Inc.

Flow–by Option 500, document 20535A., Oct. 1986.

Ellis et al., "Noninvasive Ventilatory Support During Sleep Improves Respiratory Failure in Kyphoscoliosis," Chest, Oct. 1988.

Bye et al., "Role of Sleep in the Development of Respiratory Failure in Neuromuscular Disease, Sleep Disorders Clinical Problems," date undetermined.

Strumpf et al., "Bi–level Positive Airway Pressure (BIPAP) A Low–Cost, Simple Method of Providing Nocturnal Assisted Ventilation," Montreal Gen. Hospital, date undetermined.

Robert et al., "Nocturnal Intermittent Positive Pressure Ventilation Through the Nasal Route in Sleep Apnea Syndrome Refractory to Continuous Positive Airway Pressure," La Presse Medicale, Dec. 19, 1987.

Mechanical Ventilatory Support Intensive Care Manual, Ch. 17, pp 87–92, Publisher & date undetermined.

Statutory Declarations and Curriculum Vita of Ellis, Sullivan and Grant, & Statutory Declaration of Daffurn, Oct. 13, 1994.

Ellis et al., "Treatment of Respiratory Failure During Sleep in Patients With Neuromuscular Disease, Positive–Pressure Ventilation Through a Nose–Mask," Am. Rev. Respir. Dis. vol. 135, pp. 148–152, 1987.

Calderini et al., "Continuous Positive Airway Pressure (CPAP) Improves Efficacy of Pressure Support (PS) Ventilation in Severe Chronic Obstructive Pulmonary Disease (COPD)," Montreal General Hospital.

Comprehensive Respiratory Nursing, A Decision Making Approach, Laurel D. Kersten, RN, Ph.D., WB Saunders Company, Harcourt Brace Jovanovich, Inc., 1989.

* cited by examiner

BREATHING GAS DELIVERY METHOD AND APPARATUS

CROSS-REFERENCE TO RELATED APPLICATIONS

This is a Continuation of U.S. patent appln. Ser. No. 08/823,855 filed Mar. 25, 1997, now U.S. Pat. No. 6,029,664; which is a Continuation of U.S. patent appln. Ser. No. 08/349,634 filed Dec. 2, 1994, now U.S. Pat. No. 5,632,269; which is a Continuation-in-part of U.S. appln. Ser. No. 07/947,156 filed Sep. 18, 1992, now U.S. Pat. No. 5,433,193; which is a Continuation-in-part of U.S. patent appln. Ser. No. 07/411,012 filed Sep. 22, 1989, now U.S. Pat. No. 5,148,802.

BACKGROUND OF THE INVENTION

The sleep apnea syndrome, and in particular obstructive sleep apnea, afflicts an estimated 4% to 9% of the general population and is due to episodic upper airway obstruction during sleep. Those afflicted with obstructive sleep apnea experience sleep fragmentation and intermittent, complete or nearly complete cessation of ventilation during sleep with potentially severe degrees of oxyhemoglobin unsaturation. These features may be translated clinically into debilitating daytime sleepiness, cardiac disrhythmias, pulmonary-artery hypertension, congestive heart failure and cognitive dysfunction. Other sequelae of sleep apnea include right ventricular dysfunction with cor pulmonale, carbon dioxide retention during wakefulness as well as during sleep, and continuous reduced arterial oxygen tension. Hypersomnolent sleep apnea patients may be at risk for excessive mortality from these factors as well as from an elevated risk for accidents such as while driving or operating other potentially dangerous equipment.

Although details of the pathogenesis of upper airway obstruction in sleep apnea patients have not been fully defined, it is generally accepted that the mechanism includes either anatomic or functional abnormalities of the upper airway which result in increased air flow resistance. Such abnormalities may include narrowing of the upper airway due to suction forces evolved during inspiration, the effect of gravity pulling the tongue back to appose the pharyngeal wall, and/or insufficient muscle tone in the upper airway dilator muscles. It has also been hypothesized that a mechanism responsible for the known association between obesity and sleep apnea is excessive soft tissue in the anterior and lateral neck which applies sufficient pressure on internal structures to narrow the airway.

The treatment of sleep apnea has included such surgical interventions as uvalopalatopharyngoplasty, gastric surgery for obesity, and maxillo-facial reconstruction. Another mode of surgical intervention used in the treatment of sleep apnea is tracheostomy. These treatments constitute major undertakings with considerable risk of post-operative morbidity if not mortality. Pharmacologic therapy has in general been disappointing, especially in patients with more than mild sleep apnea. In addition, side effects from the pharmacologic agents that have been used are frequent. Thus, medical practitioners continue to seek non-invasive modes of treatment for sleep apnea with high success rates and high patient compliance including, for example in cases relating to obesity, weight loss through a regimen of exercise and regulated diet.

Recent work in the treatment of sleep apnea has included the use of continuous positive airway pressure (CPAP) to maintain the airway of the patient in a continuously open state during sleep. For example, U.S. Pat. No. 4,655,213 and Australian patent AU-B-83901/82 both disclose sleep apnea treatments based on continuous positive airway pressure applied within the airway of the patient.

Also of interest is U.S. Pat. No. 4,773,411 which discloses a method and apparatus for ventilatory treatment characterized as airway pressure release ventilation and which provides a substantially constant elevated airway pressure with periodic short term reductions of the elevated airway pressure to a pressure magnitude no less than ambient atmospheric pressure.

Publications pertaining to the application of CPAP in treatment of sleep apnea include the following:

1. Lindsay, DA, Issa FG, and Sullivan C.E. "Mechanisms of Sleep Desaturation in Chronic Airflow Limitation Studied with Nasal Continuous positive Airway pressure (CPAP)", *Am Rev Respir Dis,* 1982; 125: p.112.

2. Sanders M H, Moore S E, Eveslage J. "CPAP via nasal mask: A treatment for occlusive sleep apnea", *Chest,* 1983; 83: pp. 144–145.

3. Sullivan C E, Berthon-Jones M, Issa F G. "Remission of severe obesity-hypoventilation syndrome after short-term treatment during sleep with continuous positive airway pressure", *Am Rev Respir Dis,* 1983; 128: pp. 177–181.

4. Sullivan C E, Issa F G, Berthon-Jones M, Eveslage. "Reversal of obstructive sleep apnea by continuous positive airway pressure applied through the nares", *Lancet,* 1981; 1: pp. 862–865.

5. Sullivan C E, Berthon-Jones M. Issa F G. "Treatment of obstructive apnea with continuous positive airway pressure applied through the nose", *Am Rev Respir Dis,* 1982; 125: p.107. Annual Meeting Abstracts.

6. Rapoport D M, Sorkin B, Garay S M, Goldring R H. "Reversal of the 'pickwickian Syndrome' by long-term use of nocturnal nasal-airway pressure", *N Engl J. Med,* 1982; 307: pp.931–9:33.

7. Sanders M H, Holzer B C, pennock B E. "The effect of nasal CPKP on various sleep apnea patterns", *Chest,* 1983; 84: p.336.

Presented at the Annual Meeting of the American College of Chest physicians, Chicago Ill., October 1983.

Although CPAP has been found to be very effective and well accepted, it suffers from some of the same limitations, although to a lesser degree, as do the surgical options; specifically, a significant proportion of sleep apnea patients do not tolerate CPAP well. Thus, development of other viable non-invasive therapies has been a continuing objective in the art.

BRIEF SUMMARY OF THE INVENTION

The present invention contemplates a novel and improved method for treatment of sleep apnea as well as novel methodology and apparatus for carrying out such improved treatment method. The invention contemplates the treatment of sleep apnea through application of pressure at variance with ambient atmospheric pressure within the upper airway of the patient in a manner to promote dilation of the airway to thereby relieve upper airway occlusion during sleep.

In one embodiment of the invention, positive pressure is applied alternately at relatively higher-and lower pressure levels within the airway of the patient so that the pressure-induced force applied to dilate the patient's airway is alternately a larger and a smaller magnitude dilating force. The higher and lower magnitude positive pressures are initiated by spontaneous patient respiration with the higher magnitude pressure being applied during inspiration and the lower magnitude pressure being applied during expiration.

The invention further contemplates a novel and improved apparatus which is operable in accordance with a novel and improved method to provide sleep apnea treatment. More specifically, a flow generator and an adjustable pressure controller supply air flow at a predetermined, adjustable pressure to the airway of a patient through a flow transducer. The flow transducer generates an output signal which is then conditioned to provide a signal proportional to the instantaneous flow rate of air to the patient. The instantaneous flow rate signal is fed to a low pass filter which passes only a signal indicative of the average flow rate over time. The average flow rate signal typically would be expected to be a value representing a positive flow as the system is likely to have at least minimal leakage from the patient circuit (e.g. small leaks about the perimeter of the respiration mask worn by the patient). The average flow signal is indicative of leakage because the summation of all other components of flow over time must be essentially zero since inspiration flow must equal expiration flow volume over time, that is, over a period of time the volume of air breathed in equals the volume of the gases breathed out.

Both the instantaneous flow signal and the average flow rate signal are fed to an inspiration/expiration decision module which is, in its simplest form, a comparator that continually compares the input signals and provides a corresponding drive signal to the pressure controller. In general, when the instantaneous flow exceeds average flow, the patient is inhaling and the drive signal supplied to the pressure controller sets the pressure controller to deliver air, at a preselected elevated pressure, to the airway of the patient. Similarly, when the instantaneous flow rate is less than the average flow rate, the patient is exhaling and the decision circuitry thus provides a drive signal to set the pressure controller to provide a relatively lower magnitude of pressure in the airway of the patient. The patient's airway thus is maintained open by alternating higher and lower magnitudes of pressure which are applied during spontaneous inhalation and exhalation, respectively, As has been noted, some sleep apnea patients do not tolerate standard CPAP therapy. Specifically, approximately 25% of patients cannot tolerate CPAP due to the attendant discomfort. CPAP mandates equal pressures during both inhalation and exhalation. The elevated pressure during both phases of breathing may create difficulty in exhaling and the sensation of an inflated chest. However, we have determined that although both inspiratory and expiratory air flow resistances in the airway are elevated during sleep preceding the onset of apnea, the airway flow resistance may be less during expiration than during inspiration. Thus it follows that the bi-level CPAP therapy of our invention as characterized above may be sufficient to maintain pharyngeal patency during expiration even though the pressure applied during expiration is not as high as that needed to maintain pharyngeal patency during inspiration. In addition, some patients may have increased upper airway resistance primarily during inspiration with resulting adverse physiologic consequences. Thus, our invention also contemplates applying elevated pressure only during inhalation thus eliminating the need for global (inhalation and exhalation) increases in airway pressure. The relatively lower pressure applied during expiration may in some cases approach or equal ambient pressure. The lower pressure applied in the airway during expiration enhances patient tolerance by alleviating some of the uncomfortable sensations normally associated with CPAP.

Under prior CPAP therapy, pressures as high as 20 cm H2O have been required, and some patients on nasal CPAP thus have been needlessly exposed to unnecessarily high expiratory pressures with the attendant discomfort and elevated mean airway pressure, and theoretic risk of barotrauma. Our invention permits independent application of a higher inspiratory airway pressure in conjunction with a lower expiratory airway pressure in order to provide a therapy which is better tolerated by the 25% of the patient population which does not tolerate CPAP therapy, and which may be safer in the other 75% of the patient population.

As has been noted hereinabove, the switch between higher and lower pressure magnitudes can be controlled by spontaneous patient respiration, and the patient thus is able to independently govern respiration rate and volume. As has been also noted, the invention contemplates automatic compensation for system leakage whereby nasal mask fit and air flow system integrity are of less consequence than in the prior art. In addition to the benefit of automatic leak compensation, other important benefits of the invention include lower mean airway pressures for the patient and enhanced safety, comfort and tolerance.

It is accordingly one object of the present invention to provide a novel and improved method for treatment of sleep apnea.

A further object of the invention to provide a novel and improved apparatus which is operable according to a novel methodology in carrying out such a treatment for sleep apnea.

Another object of the invention is to provide a method and apparatus for treating sleep apnea by application of alternately high and low magnitudes of pressure in the airway of the patient with the high and low pressure magnitudes being initiated by spontaneous patient respiration.

Another object of the invention is to provide an apparatus for generating alternately high and low pressure gas flow to a consumer of the gas with the higher and lower pressure flows being controlled by comparison of the instantaneous flow rate to the gas consumer with the average flow rate to the consumer, which average flow rate may include leakage from the system, and whereby the apparatus automatically compensates for system leakage.

These and other objects and further advantages of the invention will be more readily appreciated upon consideration of the following detailed description and accompanying drawings, in which.

Figure 1:
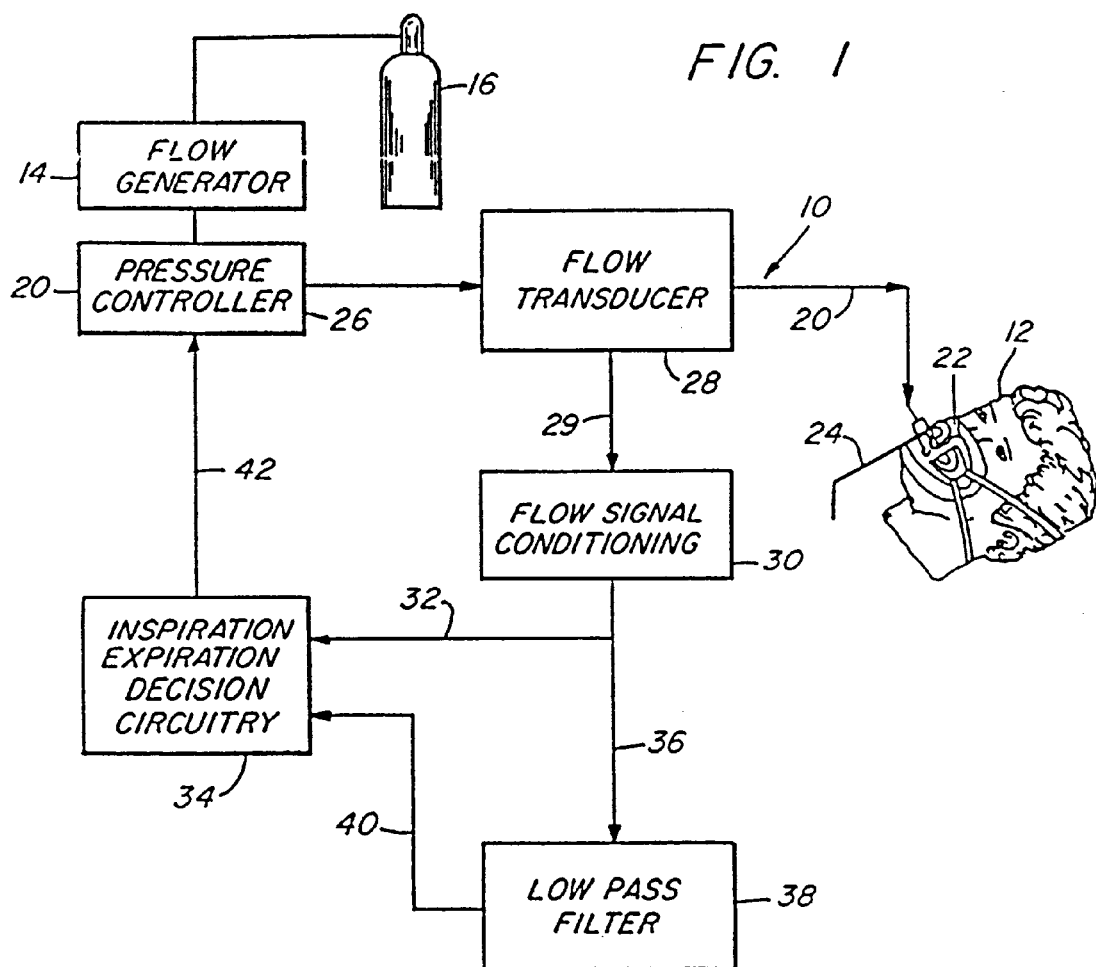
FIG. 1 is a functional block diagram of an apparatus according to the instant invention which is operable according to the method of the instant invention.

There is generally indicated at 10 in FIG. 1 an apparatus according to one presently preferred embodiment of the instant invention and shown in the form of a functional block diagram. Apparatus 10 is operable according to a novel process which is another aspect of the instant invention for delivering breathing gas such as air alternately at relatively higher and lower pressures (i.e., equal to or above ambient atmospheric pressure) to a patient 12 for treatment of the condition known as sleep apnea.

Apparatus 10 comprises a gas flow generator 14 (e.g., a blower) which receives breathing gas from any suitable source, a pressurized bottle 16 or the ambient atmosphere, for example. The gas flow from flow generator 14 is passed via a delivery conduit 20 to a breathing appliance such as a mask 22 of any suitable known construction which is worn by patient 12. The mask 22 may preferably be a nasal mask or a full face mask 22 as shown. Other breathing appliances which may be used in lieu of a mask include nasal cannulae, an endotracheal tube, or any other suitable appliance for interfacing between a source of breathing gas and a patient, consistent with the desired effect to be achieved through use of the apparatus 10.

The mask 22 includes a suitable exhaust port means, schematically indicated at 24, for exhaust of breathing gases during expiration. Exhaust port 24 preferably is a continuously open port which imposes a suitable flow resistance upon exhaust gas flow to permit a pressure controller 26, located in line with conduit 20 between flow generator 14 and mask 22, to control the pressure of air flow within conduit 20 and thus within the airway of the patient 12. For example, exhaust port 24 may be of sufficient cross-sectional flow area to sustain a continuous exhaust flow of approximately 15 liters per minute. The flow via exhaust port 24 is one component, and typically the major component of the overall system leakage, which is an important parameter of system operation. In an alternative embodiment to be discussed hereinbelow, it has been found that a non-rebreathing valve may be substituted for the continuously open port 24.

The pressure controller 26 is operative to control the pressure of breathing gas within the conduit 20 and thus within the airway of the patient. Pressure controller 26 is located preferably, although not necessarily, downstream of flow generator 14 and may take the form of an adjustable valve which provides a flow path which is open to the ambient atmosphere via a restricted opening, the valve being adjustable to maintain a constant pressure drop across the opening for all flow rates and thus a constant pressure within conduit 20.

Also interposed in line with conduit 20, preferably downstream of pressure controller 26, is a suitable flow transducer 28 which generates an output signal that is fed as indicated at 29 to a flow signal conditioning circuit 30 for derivation of a signal proportional to the instantaneous flow rate of breathing gas within conduit 20 to the patient.

It will be appreciated that flow generator 14 is not necessarily a positive displacement device. It may be, for example, a blower which creates a pressure head within conduit 20 and provides air flow only to the extent required to maintain that pressure head in the presence of patient breathing cycles, the exhaust opening 24, and action of pressure controller 26 as above described. Accordingly, when the patient is exhaling, peak exhalation flow rates from the lungs may far exceed the flow capacity of exhaust port 24. As a result, exhalation gas backflows within conduit 20 through flow transducer 28 and toward pressure controller 26, and the instantaneous flow rate signal from transducer 28 thus will vary widely within a range from relatively large positive (i.e. toward the patient) flow to relatively large negative (i.e. from the patient)-flow.

The instantaneous flow rate signal from flow signal conditioning circuitry 30 is fed as indicated at 32 to a decision module 34, a known comparator circuit for example, and is additionally fed as indicated at 36 to a low pass filter 38. Low pass filter 38 has a cut-off frequency low enough to remove from the instantaneous flow rate input signal most variations in the signal which are due to normal breathing. Low pass filter 38 also has a long enough time constant to ensure that spurious signals, aberrant flow patterns and peak instantaneous flow rate values will not dramatically affect system average flow. That is, the time constant of low pass filter 38 is selected to be long enough that it responds slowly to the instantaneous flow rate signal input. Accordingly, most instantaneous flow rate input signals which could have a large impact on system average flow in the short term have a much smaller impact over a longer term, largely because such instantaneous flow rate signal components will tend to cancel over the longer term. For example, peak instantaneous flow rate values will tend to be alternating relatively large positive and negative flow values corresponding to peak inhalation and exhalation flow achieved by the patient during normal spontaneous breathing. The output of low pass filter 38 thus is a signal which is proportional to the average flow in the system, and this is typically a positive flow which corresponds to average system leakage (including flow from exhaust 24) since, as noted, inhalation and exhalation flow cancel for all practical purposes.

The average flow signal output from the low pass filter 38 is fed as indicated at 40 to decision circuitry 34 where the instantaneous flow rate signal is continually compared to the system average flow signal. The output of the decision circuitry 34 is fed as a drive signal indicated at 42 to control the pressure controller 26. The pressure magnitude of breathing gas within conduit 20 thus is coordinated with the spontaneous breathing effort of the patient 12, as follows.

When the patient begins to inhale, the instantaneous flow rate signal goes to a positive value above the positive average flow signal value. Detection of this increase in decision circuitry 34 is sensed as the start of patient inhalation. The output signal from decision circuitry 34 is fed to pressure controller 26 which, in response, provides higher pressure gas flow within conduit 20 and thus higher pressure within the airway of the patient 12. This is the higher magnitude pressure value of our bi-level CPAP system and is referred to hereinbelow as IPAP (inhalation positive airway pressure). During inhalation, the flow rate within conduit 20 will increase to a maximum and then decrease as inhalation comes to an end.

At the start of exhalation, air flow into the patient's lungs is nil and as a result the instantaneous flow rate signal will be less than the average flow rate signal which, as noted is a relatively constant positive flow value. The decision circuitry 34 senses this condition as the start of exhalation and provides a drive signal to pressure controller 26 which, in response, provides gas flow within conduit 20 at a lower pressure which is the lower magnitude pressure value of the bi-level CPAP system, referred to hereinbelow as EPAP (exhalation positive airway pressure). As has been noted hereinabove the range of EPAP pressures may include ambient atmospheric pressure. When the patient again begins spontaneous inhalation, the instantaneous flow rate signal again increases over the average flow rate signal, and the decision circuitry once again feeds a drive signal to pressure controller 26 to reinstitute the IPAP pressure.

System operation as above specified requires at least periodic comparison of the input signals 32 and 40 by decision circuitry 34. Where this or other operations are described herein as continual, the scope of meaning to be ascribed includes both continuous (i.e. uninterrupted) and periodic (i.e. at discrete intervals).

As has been noted, the system 10 has a built-in controlled leakage via exhaust port 24 thus assuring that the average flow signal normally will be at least a small positive flow, although in some circumstances such as when oxygen is added to the gas flow, the average flow may be a negative value. During inhalation, the flow sensed by the flow transducer will be the sum of exhaust flow via port 24 and all other system leakage downstream of transducer 28, and inhalation flow within the airway of the patient 12. Accordingly, during inhalation the instantaneous flow rate signal as conditioned by conditioning module 30, will reliably and consistently reflect inhalation flow exceeding the average flow rate signal. During exhalation, the flow within conduit 20 reverses as exhalation flow from the lungs of the patient far exceeds the flow capacity of exhaust port 24. Accordingly, exhalation air backflows within conduit 20 past transducer 28 and toward pressure controller 26. Since pressure controller 26 is operable to maintain set pressure, it will act in response to flow coming from both the patient and the flow generator to open an outlet port sufficiently to accommodate the additional flow and thereby maintain the specified set pressure as determined by action of decision circuitry 34.

In both the inhalation and exhalation cycle phases, the pressure of the gas within conduit 20 exerts a pressure within the airway of the patient to maintain an open airway and thereby alleviate airway constriction.

In practice, it may be desirable to provide a slight offset in the switching level within decision circuitry 34 with respect to the average flow rate signal, so that the system does not prematurely switch from the low pressure exhalation mode to the higher pressure inhalation mode. That is, a switching setpoint offset in the positive direction from system average flow may be provided such that the system will not switch to the IPAP mode until the patient actually exerts a significant spontaneous inspiratory effort of a minimum predetermined magnitude. This will ensure that the initiation of inhalation is completely spontaneous and not forced by an artificial increase in airway pressure. A similar switching setpoint offset lay be provided when in the IPAP mode to ensure the transition to the lower pressure EPAP mode will occur before the flow rate of air into the lungs of the patient reaches zero (i.e. the switch to EPAP occurs slightly before the patient ceases inhalation.) This will ensure that the patient will encounter no undue initial resistance to spontaneous exhalation.

From the above description, it will be seen that a novel method of treating sleep apnea is proposed according to which the airway pressure of the patient is maintained at a higher positive pressure during inspiration and a relatively lower pressure during expiration, all without interference with the spontaneous breathing of the patient. The described apparatus is operable to provide such treatment for sleep apnea patients by providing a flow of breathing gas to the patient at positive pressure, and varying the pressure of the air flow to provide alternately high and low pressure within the airway of the patient coordinated with the patient's spontaneous inhalation and exhalation. The described system can also be used with pressure support systems such as the proportional airway pressure system described in U.S. Pat. No. 5,107,830 of Younes, the entire disclosure of which is hereby incorporated herein and made a part hereof by reference.

To provide pressure control, the flow rate of breathing gas to the patient is detected and processed to continually provide a signal which is proportional to the instantaneous breathing gas flow rate in the system. The instantaneous flow rate signal is further processed to eliminate variations attributable to normal patient respiration and other causes thus generating a signal which is proportional to the average or steady state system gas flow. The average flow signal is continually compared with the instantaneous flow signal as a means to detect the state of the patient's spontaneous breathing versus average system flow. When instantaneous flow exceeds the average flow, the patient is inhaling, and in response the pressure of gas flowing to the patient is set at a selected positive pressure, to provide a corresponding positive pressure within the airway of the patient. When comparison of the instantaneous flow rate signal with the average flow signal indicates the patient is exhaling, as for example when the instantaneous flow signal indicates flow equal to or less than the average flow, the pressure of breathing gas to the patient is adjusted to a selected lower pressure to provide a corresponding lower pressure within the airway of the patient.

Figure 2:
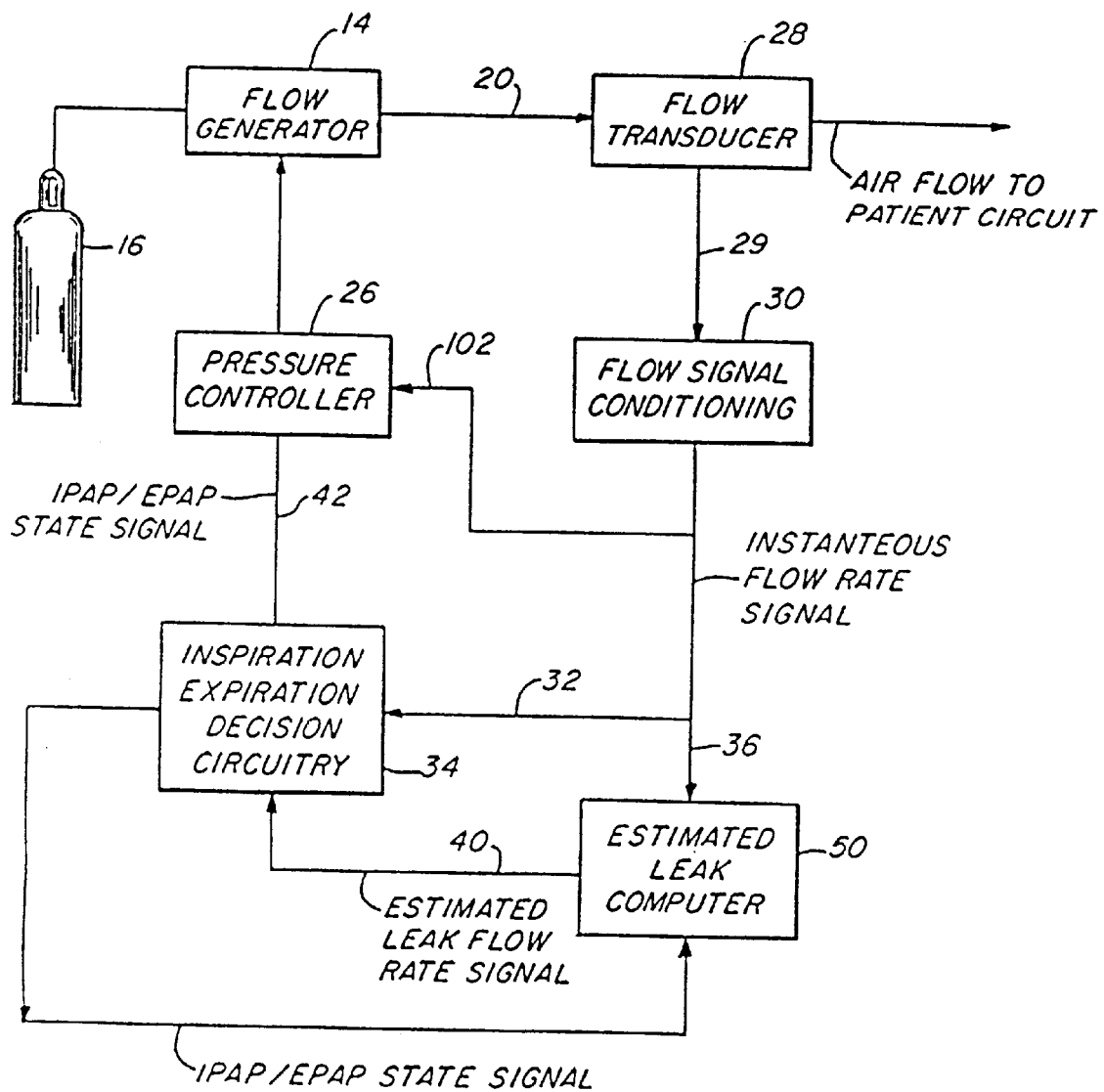
FIG. 2 is a functional block diagram showing an alternative embodiment of the invention.
Figure 3:
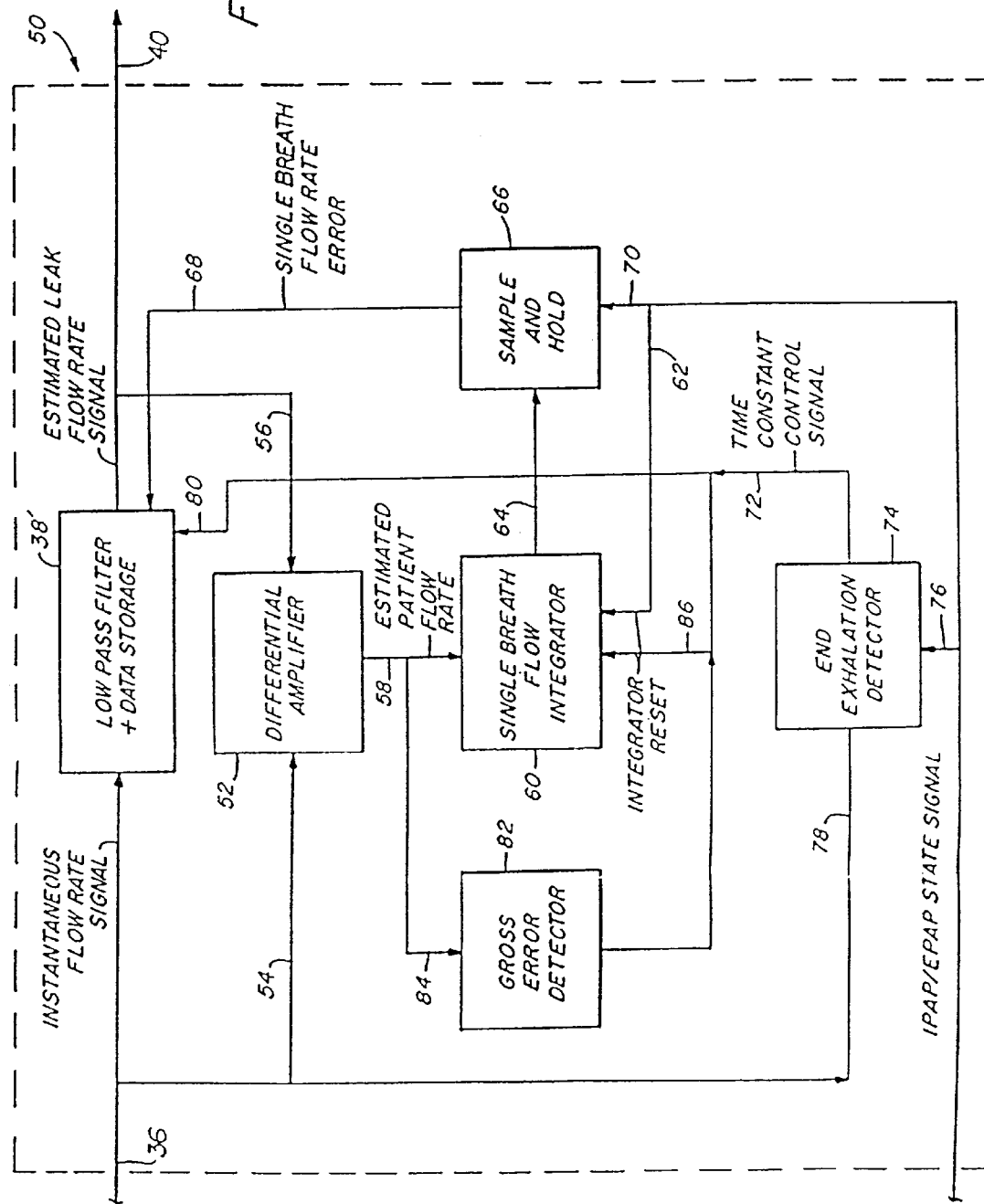
FIG. 3 is a functional block diagram of the Estimated Leak Computer of FIG. 2.

In an alternative embodiment of the invention as shown in FIGS. 2 and 3, the low pass filter 38 is replaced by an estimated leak computer which includes a low pass filter as well as other functional elements as shown in FIG. 3. The remainder of the system as shown in FIG. 2 is similar in most respects to the system shown in FIG. 1. Accordingly, like elements are identified by like numbers, and the description hereinabove of FIG. 1 embodiment also applies generally to FIG. 2.

By using the operative capability of the estimated leak computer 50, as described hereinbelow, it is possible to adjust the reference signal which is fed to decision circuitry 34 on a breath by breath basis rather than merely relying on long term average system flow. To distinguish this new reference signal from average system flow it will be referred to hereinbelow as the estimated leak flow rate signal or just the estimated leak signal.

As was noted hereinabove, the average system flow rate reference signal changes very slowly due to the long time constant of the low pass filter 38. This operative feature was intentionally incorporated to avoid disturbance of the reference signal by aberrant instantaneous flow rate signal inputs such as erratic breathing patterns. While it was possible to minimize the impact of such aberrations on the average flow rate reference signal, the average flow signal did nevertheless change, although by small increments and only very slowly in response to disturbances. Due to the long time constant of the low pass filter, such changes in the reference signal even if transitory could last for a long time.

Additionally, even a small change in the reference signal could produce a very significant effect on system triggering. For example, since the objective is to trigger the system to the IPAP mode when inhalation flow just begins to go positive, small changes in the reference signal could result in relatively large changes in the breathing effort needed to trigger the system to the IPAP mode. In some instances the change in reference signal could be so great that with normal breathing effort the patient would be unable to trigger the system. For example, if the system were turned on before placement of the mask on the face of the patient, the initial free flow of air from the unattached mask could result in a very large magnitude positive value for initial average system flow. If such value were to exceed the maximum inspiratory flow rate achieved in spontaneous respiration by the patient, the system would never trigger between the IPAP and EPAP modes because the decision circuitry would never see an instantaneous flow rate signal greater than the average flow rate signal, at least not until a sufficient number of normal breathing cycles after application of the mask to the patient to bring the reference signal down to a value more closely commensurate with the actual system leak in operation. As has been noted, with the low pass filter this could take a rather long time, during which time the patient would be breathing spontaneously against a uniform positive pressure. This would not be at all in keeping with the present invention.

In addition to the embodiment based on a reference signal derived from estimated leak flow rate on a breath by breath basis which is controlled totally by spontaneous patient breathing, two further modes of operation also are envisioned, one being spontaneous/timed operation in which the system automatically triggers to the IPAP mode for just long enough to initiate patient inspiration if the system does not sense inspiratory effort within a selected time after exhalation begins. To accomplish this, a timer is provided which is reset at the beginning of each patient inspiration whether the inspiratory cycle was triggered spontaneously or by the timer itself. Thus, only the start of inspiration is initiated by the timer. The rest of the operating cycle in this mode is controlled by spontaneous patient breathing and the circuitry of the system to be described.

A further mode of operation is based purely on timed operation of the system rather than on spontaneous patient breathing effort, but with timed cycles in place of spontaneous patient breathing.

Referring to FIG. 3, the estimated leak computer 50 includes the low pass filter 38' as well as other circuits which are operative to make corrections to the estimated leak flow rate signal based on on-going analysis of each patient breath. A further circuit is provided which is operative to adjust the estimated leak flow rate signal quickly after major changes in system flow such as when the blower has been running prior to the time when the mask is first put on the patient, or after a major leak in the system has either started or has been shut off.

The low pass filter 38' also includes a data storage capability whose function will be described hereinbelow.

The low pass filter 38' operates substantially as described above with reference to FIG. 1 in that it provides a long term average of system flow which is commensurate with steady state system leakage including the flow capacity of the exhaust port 24. This long term average is operative in the FIG. 3 embodiment to adjust the estimated leak flow rate reference signal only when system flow conditions are changing very slowly.

To provide breath by breath analysis and adjustment of the reference signal, a differential amplifier 52 receives the instantaneous flow rate signal as indicated at 54, and the estimated leak signal output from low pass filter 38' as indicated at 56.

The output of differential amplifier 52 is the difference between instantaneous flow rate and estimated leak flow rate, or in other words estimated instantaneous patient flow rate. This will be clear upon considering that instantaneous flow is the sum of patient flow plus actual system leakage. The estimated patient flow signal output from differential amplifier 52 is provided as indicated at 58 to a flow integrator 60 which integrates estimated patient flow breath by breath beginning and ending with the trigger to IPAP. Accordingly, an additional input to the flow integrator 60 is the IPAP/EPAP state signal as indicated at 62. The IPAP/EPAP state signal is the same as the drive signal provided to pressure controller 26; that is, it is a signal indicative of the pressure state, as between IPAP and EPAP, of the system. The state signal thus may be used to mark the beginning and end of each breath for purposes of breath by breath integration by integrator 60.

If the estimated leak flow rate signal from low pass filter 38' is equal to the true system leak flow rate, and if the patient's inhaled and exhaled volumes are identical for a given breath (i.e. total positive patient flow equals total negative patient flow for a given breath), then the integral calculated by integrator 60 will be zero and no adjustment of estimated leak flow rate will result. When the integral calculated by integrator 60 is non-zero, the integral value in the form of an output signal from integrator 60 is provided as indicated at 64 to a sample and hold module 66. Of course, even with a zero value integral, an output signal may be provided to module 66, but the ultimate result will be no adjustment of the estimated leak flow rate signal.

A non-zero integral value provided to module 66 is further provided to module 38' as indicated at 68 with each patient breath by operative action of the IPAP/EPAP state signal upon module 66 as indicated at 70. The effect of a non-zero integral value provided to module 38' is an adjustment of the estimated leak flow rate signal proportional to the integral value and in the direction which would reduce the integral value towards zero on the next breath if all other conditions remain the same.

With this system, if the patient's net breathing cycle volume is zero, and if the system leak flow rate changes, the integrator circuit will compensate for the change in leak flow rate by incremental adjustments to the estimated leak flow rate within several patient breaths.

The integrator circuit 60 also will adjust the estimated leak flow rate signal in response to non-zero net volume in a patient breathing cycle. It is not unusual for a patient's breathing volume to be non-zero. For example, a patient may inhale slightly more on each breath than he exhales over several breathing cycles, and then follow with a deeper or fuller exhalation. In this case, the integrator circuit would adjust the estimated leak flow rate signal as if the actual system leak rate had changed; however, since the reference signal correction is only about one tenth as large as would be required to make the total correction in one breath, the reference signal will not change appreciably over just one or two breaths. Thus, the integrator circuit accommodates both changes in system leakage and normal variations in patient breathing patterns.

An end exhalation module 74 is operative to calculate another data component for use in estimating the system leak flow rate as follows. The module 74 monitors the slope of the instantaneous flow rate wave form. When the slope value is near zero during exhalation (as indicated by the state signal input 76) the indication is that the flow rate is not changing. If the slope of the instantaneous flow rate signal wave form remains small after more than one second into the respiratory phase, the indication is that exhalation has ended and that the net flow rate at this point thus is the leak flow rate. However, if estimated patient flow rate is non-zero at the same time, one component of the instantaneous flow rate signal must be patient flow.

When these conditions are met, the circuit adjusts the estimated leak flow rate slowly in a direction to move estimated patient flow rate toward zero to conform to instantaneous patient flow conditions expected at the end of exhalation. The adjustment to estimated leak flow rate is provided as an output from module 74 to low pass filter 38' as indicated at 80. When this control mechanism takes effect, it disables the breath by breath volume correction capability of integrator circuit 60 for that breath only.

The output of module 74 is a time constant control signal which is provided to low pass filter 38' to temporarily shorten the time constant thereof for a sufficient period to allow the estimated leak flow rate to approach the instantaneous flow rate signal at that specific instant. It will be noted that shortening the low pass filter time constant increases the rapidity with which the low pass filter output (a system average) can adjust toward the instantaneous flow rate signal input.

Another component of estimated leak flow rate control is a gross error detector 82 which acts when the estimated patient flow rate, provided thereto as indicated at 84, is away from zero for more than about 5 seconds. Such a condition may normally occur, for example, when the flow generator 14 is running before mask 22 is applied to the patient. This part of the control system is operative to stabilize operation quickly after major changes in the leak rate occur.

In accordance with the above description, it will be seen that low pass filter 38' acts on the instantaneous flow rate signal to provide an output corresponding to average system flow, which is system leakage since patient inspiration and expiration over time constitutes a net positive flow of zero. With other enhancements, as described, the system average flow can be viewed as an estimate of leakage flow rate.

The differential amplifier 52 processes the instantaneous flow rate signal and the estimated leak flow rate signal to provide an estimated patient flow rate signal which is integrated and non-zero values of the integral are fed back to module 38' to adjust the estimated leak flow rate signal on a breath by breath basis. The integrator 60 is reset by the IPAP/EPAP state signal via connection 62.

Two circuits are provided which can override the integrator circuit, including end exhalation detector 74 which provides an output to adjust the time constant of low pass filter 38' and which also is provided as indicated at 86 to reset integrator 60. Gross error detector 82 is also provided to process estimated patient flow rate and to provide an adjustment to estimated leak flow rate under conditions as specified. The output of module 82 also is utilized as an integrator reset signal as indicated at 86. It will be noted that the integrator 60 is reset with each breath of the patient if, during that breath, it is ultimately overridden by module 74 or 82. Accordingly, the multiple reset capabilities for integrator 60 as described are required.

In operation, the system may be utilized in a spontaneous triggering mode, a spontaneous/timed mode or a purely timed mode of operation. In spontaneous operation, decision circuitry 34 continuously compares the instantaneous flow rate with estimated leak flow rate. If the system is in the EPAP state or mode, it remains there until instantaneous flow rate exceeds estimated leak flow rate by approximately 40 cc per second. When this transition occurs, decision circuitry 34 triggers the system into the IPAP mode for 150 milliseconds. The system will then normally remain in the IPAP mode as the instantaneous flow rate to the patient will continue to increase during inhalation due to spontaneous patient effort and the assistance of the increased IPAP pressure.

After the transition to the IPAP mode in each breath, a temporary offset is added to the estimated leak flow rate reference signal. The offset is proportional to the integral of estimated patient flow rate beginning at initiation of the inspiratory breath so that it gradually increases with time during inspiration at a rate proportional to the patient's inspiratory flow rate. Accordingly, the flow rate level above estimated leak flow needed to keep the system in the IPAP mode during inhalation decreases with time from the beginning of inhalation and in proportion to the inspiratory flow rate. With this enhancement, the longer an inhalation cycle continues, the larger is the reference signal below which instantaneous flow would have to decrease in order to trigger the EPAP mode. For example, if a patient inhales at a constant 500 cc per second until near the end of inspiration, a transition to EPAP will occur when his flow rate drops to about 167 cc per second after one second, or 333 cc per second after two seconds, or 500 cc per second after three seconds, and so forth. For a patient inhaling at a constant 250 cc per second, the triggers would occur at 83, 167 and 250 cc per second at one, two and three seconds into IPAP, respectively.

In this way, the EPAP trigger threshold comes up to meet the inspiratory flow rate with the following benefits. First, it becomes easier and easier to end the inspiration cycle with increasing time into the cycle. Second, if a leak develops which causes an increase in instantaneous flow sufficient to trigger the system into the IPAP mode, this system will automatically trigger back to the EPAP mode after about 3.0 seconds regardless of patient breathing effort. This would allow the volume-based leak correction circuit (i.e. integrator 60) to act as it is activated with each transition to the IPAP mode. Thus, if a leak develops suddenly, there will be a tendency toward automatic triggering rather than spontaneous operation for a few breaths, but the circuit will not be locked into the IPAP mode.

Upon switching back to the EPAP mode, the trigger threshold will remain above the estimated leak flow rate for approximately 500 milliseconds to allow the system to remain stable in the EPAP mode without switching again while the respective flow rates are changing. After 500 milliseconds, the trigger threshold offset is reset to zero to await the next inspiratory effort.

The normal state for the circuit is for it to remain in the EPAP mode until an inspiratory effort is made by the patient. The automatic corrections and adjustments to the reference signal are effective to keep the system from locking up in the IPAP mode and to prevent auto-triggering while at the same time providing a high level of sensitivity to inspiratory effort and rapid adjustment for changing leak conditions and breathing patterns.

In the spontaneous/timed mode of operation, the system performs exactly as above described with reference to spontaneous operation, except that it allows selection of a minimum breathing rate to be superimposed upon the spontaneous operating mode. If the patient does not make an inspiratory effort within a predetermined time, the system will automatically trigger to the IPAP mode for 200 milliseconds. The increased airway pressure for this 200 milliseconds will initiate patient inspiration and provide sufficient time that spontaneous patient flow will exceed the reference signal so that the rest of the cycle may continue in the spontaneous mode as above described. The breaths per minute timer is reset by each trigger to IPAP whether the transition was triggered by the patient or by the timer itself.

In the timed operating mode, 411 triggering between IPAP and EPAP modes is controlled by a timer with a breaths per minute control being used to select a desired breathing rate from, for example, 3 to 30 breaths per minute. If feasible, the selected breathing rate is coordinated to the patient's spontaneous breathing rate. The percent IPAP control is used to set the fraction of each breathing cycle to be spent in the IPAP mode. For example, if the breaths per minute control is set to 10 breaths per minute (6 seconds per breath) and the percent IPAP control is set to 33%, then the flow generator will spend, in each breathing cycle, two seconds in IPAP and four seconds in EPAP.

Figure 4:
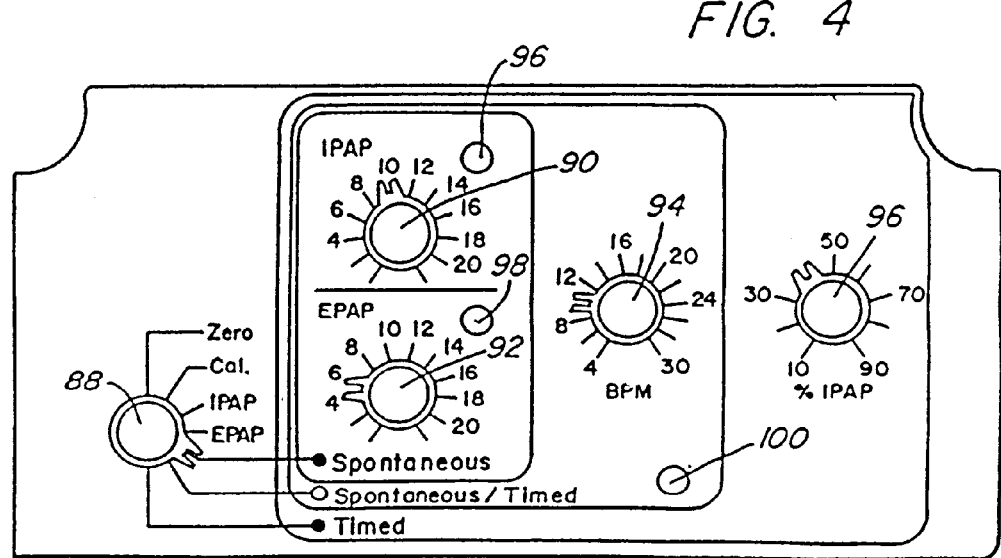
FIG. 4 is a frontal elevation of a control panel for the apparatus of this invention.

FIG. 4 illustrates a control panel for controlling the system above described and including a function selector switch which includes function settings for the three operating modes of spontaneous, spontaneous/timed, and timed as above described. The controls for spontaneous mode operation include IPAP and EPAP pressure adjustment controls 90 and 92, respectively. These are used for setting the respective IPAP and EPAP pressure levels. In the spontaneous/timed mode of operation, controls 90 and 92 are utilized as before to set IPAP and EPAP pressure levels, and breaths per minute control 94 additionally is used to set the minimum desired breathing rate in breaths per minute. In the timed mode of operation, controls 90, 92 and 94 are effective, and in addition the percent IPAP control 96 is used to set the time percentage of each breath to be spent in the IPAP mode.

Lighted indicators such as LED's 96, 98 and 100 are also provided to indicate whether the system is in the IPAP or EPAP state, and to indicate whether in the spontaneous/timed mode of operation the instantaneous state of the system is spontaneous operation or timed operation.

Figure 5:
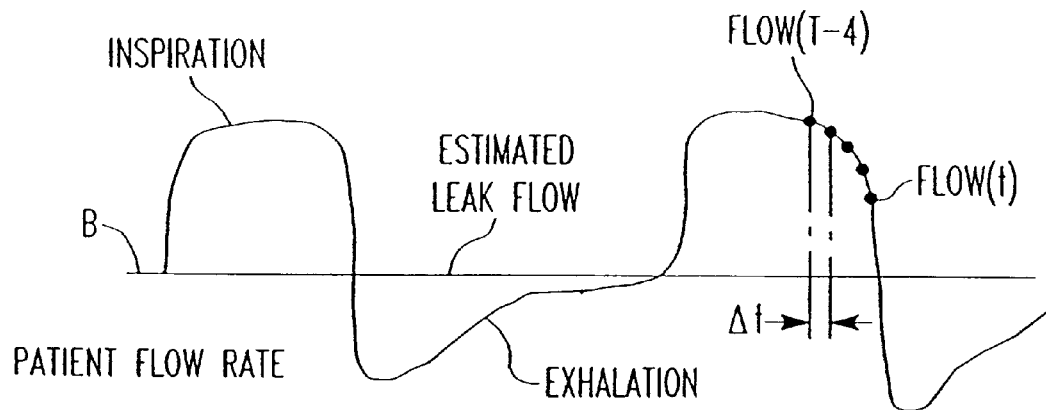
FIG. 5 is a trace of patient flow rate versus time pertaining to another embodiment of the invention.

An alternative embodiment of the invention contemplates detecting the beginning of inspiration and expiration by reference to a patient flow rate wave form such as shown in FIG. 5. Comparison of instantaneous flow rate with average flow rate as set forth hereinabove provides a satisfactory method for determining whether a patient is inhaling or exhaling; however, other means for evaluating instantaneous flow rate can also be used, and these may be used alone or in combination with average flow rate.

For example, FIG. 5 shows a typical patient flow rate wave form with inspiration or inhalation flow shown as positive flow above base line B and exhalation flow shown as negative flow below base line B. The flow rate wave form may thus be sampled at discrete time intervals. The current sample is compared with that taken at an earlier time. This approach appears to offer the benefit of higher sensitivity to patient breathing effort in that it exhibits less sensitivity to errors in the estimated system leakage, as discussed hereinabove.

Normally, the estimated inspiratory and expiratory flow rate wave forms will change slowly during the period beginning after a few hundred milliseconds into the respective inspiratory and expiratory phases, up until the respective phase is about to end. Samples of the flow rate wave form are taken periodically, and the current sample is compared repeatedly with a previous sample. During inspiration, if the magnitude of the current sample is less than some appropriate fraction of the comparison sample, then the inspiration phase is deemed to be finished. This condition thus can be used to trigger a change to the desired exhalation phase pressure. The same process can be used during exhalation to provide a trigger condition for the changeover to inhalation pressure.

Figure 6:
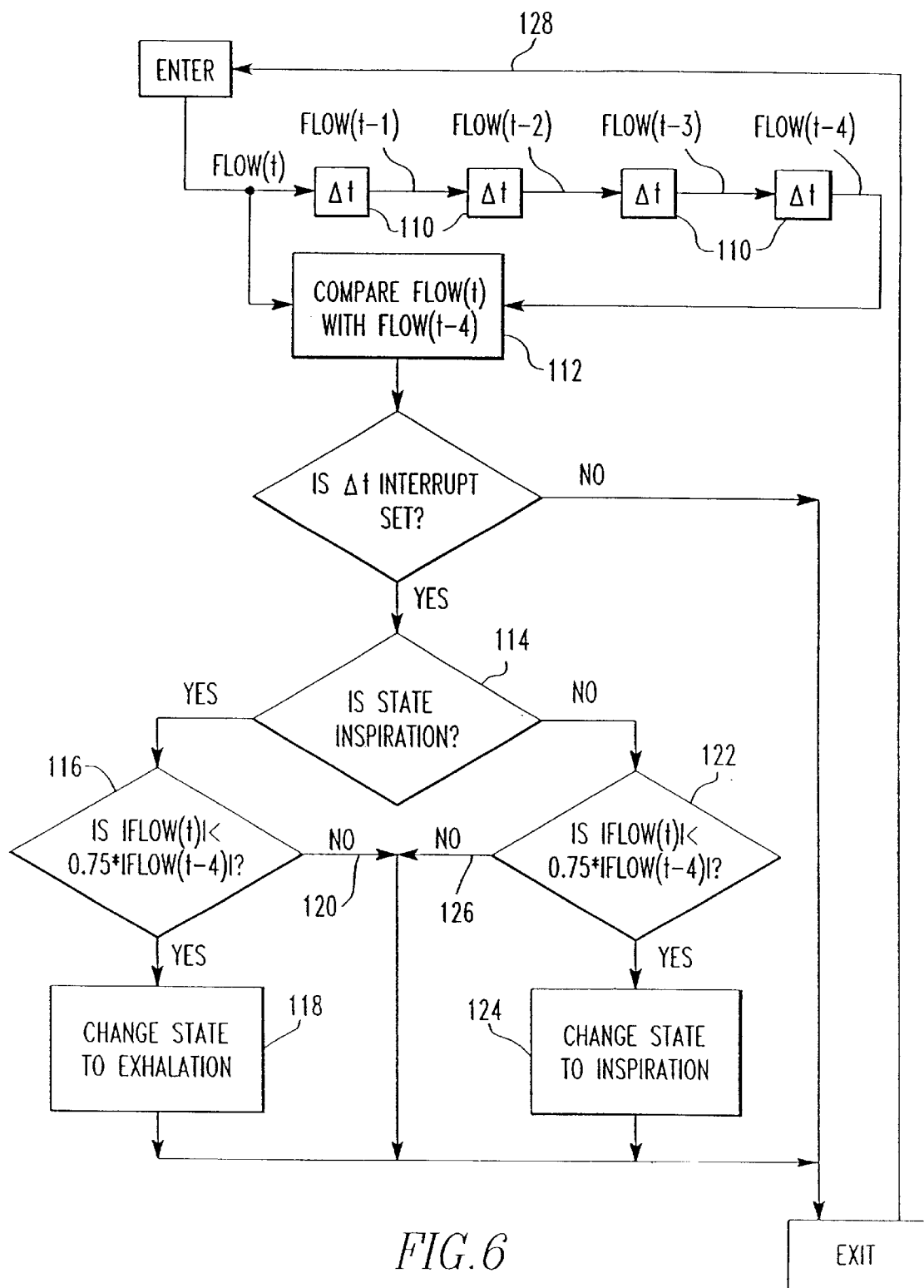
FIG. 6 is a flow diagram relating to the embodiment of FIG. 5.

FIG. 6 illustrates a flow diagram for a suitable algorithm showing repeated sampling of the patient flow rate wave form at time intervals $\Delta t$, as shown at 110, and repeated comparison of the flow at current time t with a prior sampling, for example the flow at time t-4 as indicated at 112. Of course, the time increment between successive samplings is small enough that the comparison with the value observed in the fourth prior sampling event covers a suitably small portion of the flow rate wave form. For example, as shown in FIG. 5 the designations for flow sampled at time t, the sample value taken four sampling events prior at time t-4, and the time interval $\Delta t$ illustrate one suitable proportionate relationship between 66 t and the time duration of a patient breath. This is., however, only an illustration. In fact, electronic technology such as disclosed hereinabove would be capable of performing this algorithm using much smaller $\Delta t$ intervals, provided other parameters of the algorithm, such as the identity of the comparison sample and/or the proportion relationship between the compared samples, are adjusted accordingly.

Continuing through the flow chart of FIG. 6, if the patient's state of breathing is inspiration (114), the current flow sample value is compared with the sample value observed t-4 sampling events prior. If the current flow sample value is less than, for example, 75% of the comparison flow value (116), the system triggers a change in state to the exhalation phase (118). If the current flow sample value is not less than 75% of the comparison value (120), no change in breathing state is triggered.

If the breathing state is not inspiration, and the current flow sample value is less than 75% of the selected comparison value (122), then an expiration phase, rather than an inspiration phase, is completed and the system is triggered to change the state of breathing to inspiration (124). If the specified flow condition is not met, again no change in breathing phase is triggered (126).

The routine characterized by FIG. 6 repeats continuously as indicated at 128, each time comparing a current flow sample with the fourth (or other suitable) prior sample to determine whether the system should trigger from one breathing phase to the other.

Of course, it will be understood that the embodiment set forth above with reference to FIGS. 5 and 6 does not trigger changes in breathing per se within the context of the invention as set forth in the balance of the above specification. Rather, in that context the FIG. 5 and 6 embodiment merely detects changes between inspiration and expiration in spontaneous patient breathing, and triggers the system to supply the specified higher or lower airway pressure as set forth hereinabove.

Common problems resulting from insufficient ventilator triggering sensitivity include failure of the ventilator to trigger to IPAP upon exertion of inspiratory effort by the patient, and failure of the ventilator in IPAP to trigger off or to EPAP at the end of patient inspiratory effort. Patient respiratory effort relates primarily to the inspiratory portion of the respiration cycle because in general only the inspiratory part of the cycle involves active effort. The expiratory portion of the respiration cycle generally is passive. A further characteristic of the respiratory cycle is that expiratory flow rate generally may reach zero and remain at zero momentarily before the next inspiratory phase begins. Therefore the normal stable state for a patient-triggered ventilator should be the expiratory state, which is referred to herein as EPAP.

Although the apparatus as above described provides sensitive triggering between the IPAP and EPAP modes, triggering can be still further improved. The primary objectives of improvements in triggering sensitivity generally are to decrease the tendency of a system to trigger automatically from EPAP to IPAP in the absence of inspiratory effort by the patient, and to increase system sensitivity to the end of patient inspiratory effort. These are not contradictory objectives. Decreasing auto-trigger sensitivity does not necessarily also decrease triggering sensitivity to patient effort.

Generally, for a patient whose ventilatory drive is functioning normally, the ideal ventilator triggering sensitivity is represented by close synchronization between changes of state in the patient's respiration (between inspiration and expiration), and the corresponding changes of state by the ventilator. Many conventional pressure support ventilators which trigger on the basis of specified flow or pressure thresholds can approach such close synchronization only under limited conditions.

In the system described hereinabove, where triggering is based on specified levels of estimated patient flow rate, close synchronization between system state changes and patient respiration state changes can be readily achieved. This is especially true for patients having no severe expiratory flow limitation as the flow rate reversals for such patients typically may correspond quite closely with changes in the patient respiratory effort; however, flow rate reversals may not necessarily correspond precisely to changes in patient respiratory effort for all patients. For example, those patients experiencing respiratory distress or those being ventilated with pressure support ventilation may not exhibit the desired close correspondence between patient effort and breathing gas supply flow rate reversals.

In addressing improvements in synchronized triggering based on flow rate, at least three different respiratory cycles are considered. The first is the patient respiratory cycle as indicated by patient effort. If the patient makes any effort, it must include inspiratory effort. Patient expiration may be active or passive.

The second cycle is the ventilator respiratory cycle, that is, the cycle delivered by the ventilator. This cycle also has an inspiratory phase and an expiratory phase, but the ventilator may or may not be synchronized with the corresponding phases of the patient respiratory cycle.

The third cycle is the flow respiratory cycle, as indicated by the direction of flow to or from the patient's airway. Flow passes from the ventilator into the patient on inspiration and out of the patient on expiration. If one looks at this cycle only, the inspiratory/expiratory changes could be identified by the zero flow crossings between positive and negative flow.

Ideally, if the patient's breathing drive is competent, the flow respiratory cycle should be synchronized with the patient respiratory cycle, with the assistance of the ventilator. One important objective of the triggering described here is to synchronize the ventilator cycle with the patient cycle so that the flow cycle is coordinated with patient inspiratory effort. With flow triggering the pressure delivered by the ventilator affects the flow, in addition to the effect on flow of the patient's own efforts. This is another reason why zero flow crossings may not necessarily be good indicators of changes in patient effort.

As described, flow triggering provides certain advantages not available with some other modes of ventilator triggering. For example, in ventilators which use pressure variation for triggering, when the patient makes an inspiratory effort lung volume begins to increase. This volume change causes a pressure drop, which in some conventional closed circuit ventilators is sensed by the ventilator triggering system to initiate breathing gas delivery. With flow triggering there is no need for a pressure drop to occur in the breathing circuit. The triggering algorithm may still require the patient lung volume to increase, but since the pressure in the ventilator circuit does not have to drop the patient expends less energy in the inspiratory effort to achieve a given volume change.

Additionally, in an open circuit, that is one in which exhaled gases are flushed from the system via a fixed leak, it would be difficult to generate the required pressure drop for pressure based triggering upon exertion of small patient inspiratory effort. That is, with an open circuit the magnitude of patient effort required to generate even a very small pressure drop would be considerable. Thus, it would be correspondingly quite difficult to achieve sufficient sensitivity in a pressure based triggering system to provide reliable triggering if used in conjunction with an open circuit. In general, the open circuit is simpler than one with a separate exhaust valve and exhaust tubing and therefore simpler to use and less costly, and for these and other reasons may often be preferred over a closed circuit.

In a presently preferred triggering scheme for the above described flow rate triggering system, the flow rate signal must exceed a threshold value equivalent to 40 cc per second continuously for 35 milliseconds in order to trigger the system to IPAP. If the flow rate signal drops below the specified threshold value during the specified time interval, the threshold timer is reset to zero. These threshold values permit triggering with a minimal patient volume change of only 1.4 cc, which represents much improved sensitivity over some prior pressure triggered ventilators.

In reality, however, such minimal patient volume change represents overly sensitive triggering which would not be practical in actual practice. Noise in the flow rate signal would continually reset the threshold timer during intervals when the patient flow rate is very close to 40 cc per second. Therefore, it is believed a minimum volume change for consistent triggering of the described system would be about 3 cc., although this too is considered to be a very sensitive triggering level. It is noted, however, that pressure signal noise can also occur in prior pressure triggered ventilators, thus creating triggering sensitivity problems. Due to this and other details of their operation the theoretical maximum sensitivity of such prior ventilators is better than the sensitivity which can actually be achieved in operation.

As one example of an operating detail which can adversely affect sensitivity in prior ventilators, if the ventilator response time is slow, the resulting time delay between the time when a triggering time requirement is satisfied and the time when gas supply pressure actually begins to rise will adversely affect sensitivity. During the time delay, the patient is continuing to make inspiratory effort and thus will be doing much greater actual work than that needed to trigger the ventilator, and much greater work than would be done if the ventilator responded more quickly. Another example occurs during rapid breathing when a patient begins to make an inspiratory effort before exhalation flow rate drops to zero. In this case, an additional delay occurs until flow reverses and the exhalation valve has time to close.

Triggering to EPAP upon exhalation also can present problems. A typical prior pressure support ventilator will trigger off at the end of inspiration based on the patient's flow decreasing past a flow threshold, or on timing out of a timer, for example. The trigger-to-exhalation flow threshold can be either a fixed value or a fraction of peak flow, for example 25% of peak flow. As one example of the sort of problem which can affect triggering to exhalation in prior ventilators, a patient with moderately severe COPD (chronic obstructive pulmonary disease) will exhibit comparatively high respiratory system resistance and perhaps low respiratory system elastance. This will result in a comparatively long time constant for the patient, the time constant being the time taken for exhalation flow to decay to ¼ of peak flow or other suitable selected proportion of peak flow. The long time constant for the COPD patient means that flow will drop slowly during inspiration.

The only way this patient will be able to trigger the ventilator to exhalation will be in increase exhalatory effort. That is, the patient must actively decrease the flow rate by respirator muscle effort to trigger to exhalation. Further, because of the patient's large time constant, there may be considerable exhalation flow when the patient's inspiratory cycle beings, and the trigger to IPAP thus will be delayed, to the detriment of ventilator sensitivity.

To achieve greater sensitivity to patient effort in an improved embodiment of the invention, the disclosed system may be provided with apparatus to continually monitor multiple conditions rather than monitoring only a single condition as represented by the above description pertinent to element 82. In the improved embodiment, inspiratory time is limited to no more than about 3 seconds under normal conditions, and normal exhalation flow rate is required to be nearly zero by about 5 seconds after the beginning of exhalation.

To employ the first of these conditions the system monitors estimated patient flow rate and requires its value to cross zero at least once approximately every 5 seconds. To monitor this condition, an input is required from the output of a comparator which compares patient flow rate with a zero value. The comparator is a bistable device which provides one output (i.e. true) when patient flow is greater than zero, and an alternative output (i.e. false) when patient flow is less than zero. If the comparator output is either true or false continuously for longer than about 5 seconds, a signal is generated which triggers the system to EPAP.

The second condition is the monitoring of the IPAP/EPAP state to see if it remains in EPAP for more than about 5 seconds. If it does, the volume will be held at zero until there is another valid trigger to IPAP. This function prevents the volume signal from drifting away from zero when there is an apnea. After 5 seconds in EPAP volume should normally be zero.

Further improvements in triggering sensitivity require consideration of more than flow rate levels for determination of suitable triggering thresholds. In particular, changes in the shape or slope of the patient's flow rate wave form can be utilized to better synchronize a ventilation system with spontaneous respiratory effort exerted by the patient. Some such considerations are discussed hereinabove with reference to FIGS. 5 and 6.

Figure 7:
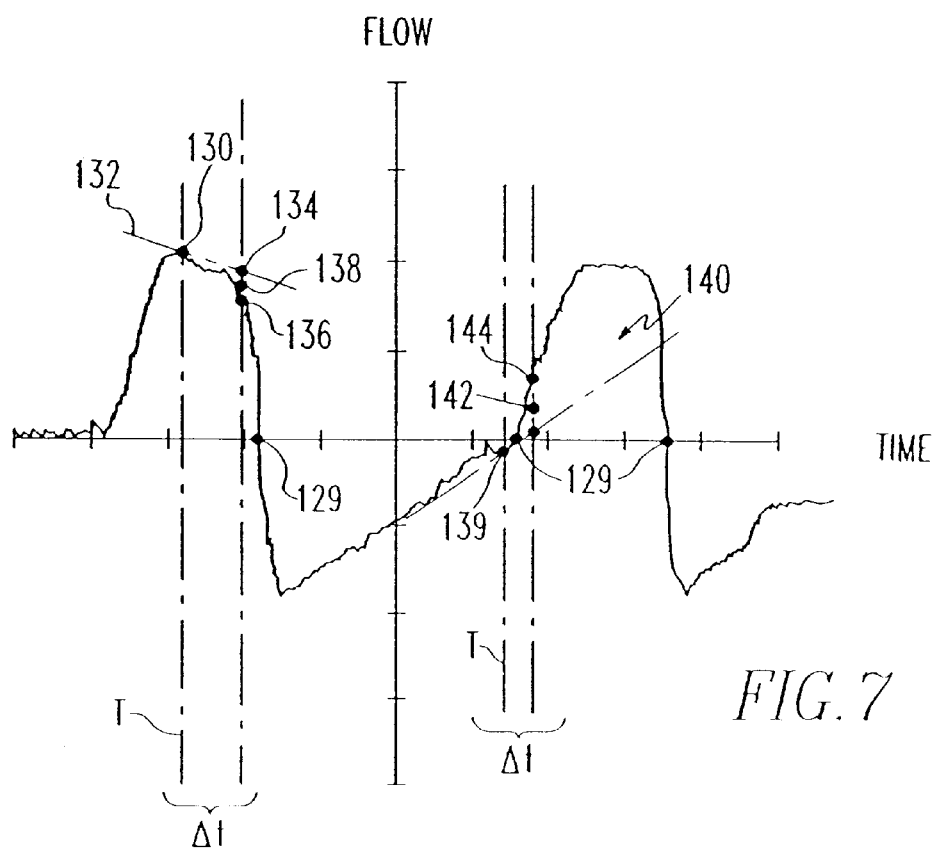
FIG. 7 is a trace of patient flow rate versus time illustrating another embodiment of the invention.

A typical flow rate tracing for a normal patient experiencing relaxed breathing is shown in FIG. 7. The simplest approach for synchronizing ventilator triggering to spontaneous patient respiration has often been to use the zero flow points 129 as the reference for triggering between EPAP and IPAP; however, this approach does not address the potential problems. First, as noted above, flow rate reversals may not necessarily correspond to changes in patient spontaneous breathing effort for all patients. Second, the flow signal is not necessarily uniform. Concerning this problem in particular, small flow variations corresponding to noise in electronic signals will occur due to random variations in system and airway pressure caused by flow turbulence or random variations in the pressure control system. Additional flow rate noise results from small oscillations in the breathing gas flow rate due to changes in blood volume within the patient's chest cavity with each heart beat. Third, since pressure support commonly is an all-or-nothing mode of ventilation, and since the respiratory systems of all patients will exhibit an elastance component, an inappropriate trigger to IPAP will always result in delivery of some volume of breathing gas unless the patient's airway is completely obstructed. Thus, reliance on zero flow or flow reversals for triggering will in many instances result in loss of synchronization between a patient inspiratory effort and ventilator delivery of breathing gas.

Referring to FIG. 7, there is shown a flow rate versus time trace for the respiratory flow of a typical, spontaneously breathing person. Time advances from left to right on the horizontal axis and flow rate varies about a zero-value base line on the vertical axis. Of course, in the description below referring to FIG. 7 it is to be understood that the illustrated flow rate versus time trace is an analog for spontaneous breathing by a patient and for any detectors or sensors, whether based on mechanical, electronic or other apparatus, for detecting patient flow rate as a function of time.

It will be noted on reference to FIG. 7 that relatively sharp breaks or slope changes occur in the flow rate trace when patient inhalation effort begins and ends. Thus, although the slope of the flow rate trace may vary widely from patient to patient depending on the patient resistance and elastance, for any given patient it will tend to be relatively constant during inhalation and exhalation. The relatively sudden increase in flow trace slope when an inspiratory effort begins, and a corresponding sudden decrease in slope when inspiratory effort ends, can be used to identify IPAP and EPAP trigger points. Since the abrupt changes in flow trace slope at the beginning and end of inhalation correspond with the beginning and end of inspiratory effort, the flow trace slope or shape may be used to trigger the system between the IPAP and EPAP state in reliance on changes in patient effort rather than on relatively fixed flow thresholds.

The basic algorithm for operation of this further improved triggering system is as follows. The input to the system is the current flow rate at any point on the flow trace, for example point 130 in FIG. 7. The flow value is differentiated to get the corresponding current slope 132 of the flow function at time T. Of course, the slope corresponds to the instantaneous rate of change of flow rate.

The slope 132 is scaled by a time factor $\Delta t$, and is then added to the current flow value. This gives a prediction of the flow 134 at a future time $t+\Delta t$, based on the current slope 132 of the flow trace. As noted, the magnitude of time interval $\Delta t$ is determined by the selected scale factor by which slope 132 is scaled. The resulting flow prediction 134 assumes, effectively, a uniform rate of change for the flow throughout the period $\Delta t$. It will be understood that in FIG. 7 the magnitude of time intervals 66 is exaggerated, and is different for the end of inspiration and beginning of inspiration changes, to facilitate clear illustration. In practice, $\Delta t$ may be approximately 300 milliseconds, for example.

The accuracy of the predicted future flow rate value 134 will depend upon the actual, varying slope of the flow trace during time interval Δt as compared to the presumed uniform slope 132. To the extent that the flow trace during interval Δt deviates from slope 132, the actual flow value 136 at the end of time interval Δt will vary from the predicted flow value 134. Accordingly, it may be seen that the effectiveness of this algorithm depends upon the actual deviation in the flow trace from slope 132 during any given Δt time interval being small except when the patient makes a significant change in respiratory effort.

To further modify the predicted flow 134, an offset factor may be added to it to produce an offset predicted value 138. The offset is negative during inspiration so that the predicted flow at time t+Δt will be held below the actual flow at t+Δt except when the flow trace changes in the decreasing flow direction, such as would occur at the end of inspiration when patient effort ceases or even reverses.

The above description refers to an end-of-inspiration trigger to EPAP. In an entirely similar fashion, as indicated generally at 140 in FIG. 7, a trigger to IPAP can be governed by prediction of a future flow rate based on differentiation of an instantaneous flow rate 139 plus an offset factor to provide a predicted flow rate value 142. It is noted that in this instance the offset factor will be a positive offset since it is an abruptly increasing flow rate that one would wish to detect. In this instance, when actual flow rate increases sufficiently during the Δt interval to exceed predicted value 142, for example as indicated at 144, the system will trigger to IPAP. Thus, at any point in the flow cycle when actual flow after a predetermined time interval Δt differs sufficiently from the predicted, offset flow value based on flow trace slope at time T, the system is triggered to IPAP or EPAP depending upon the direction, either positive or negative, in which actual flow varies from the predicted flow.

The flow rate prediction based on current flow trace slope, and the comparison of the predicted flow rate with actual flow rate as described, is repeated at a high rate to generate a continuous or nearly continuous stream of actual flow-to-predicted flow comparisons. For example, in an analog system the process is continuous, while in a digital system the process is repeated every 10 milliseconds or faster. In the resulting locus of predicted flow value points, most actual-to-predicted flow comparisons do not result in triggering because actual flow rate does not deviate sufficiently from the predicted rate. Only at the inspiratory/expiratory changes does this occur. The result is a triggering method which, because it is based on flow predictions, does not require changes in patient inspiratory effort to achieve triggering in synchronism with spontaneous patient respiration. Of course, the described differentiation technique of flow prediction is but one example of a suitable flow wave shape triggering algorithm.

Figure 8:
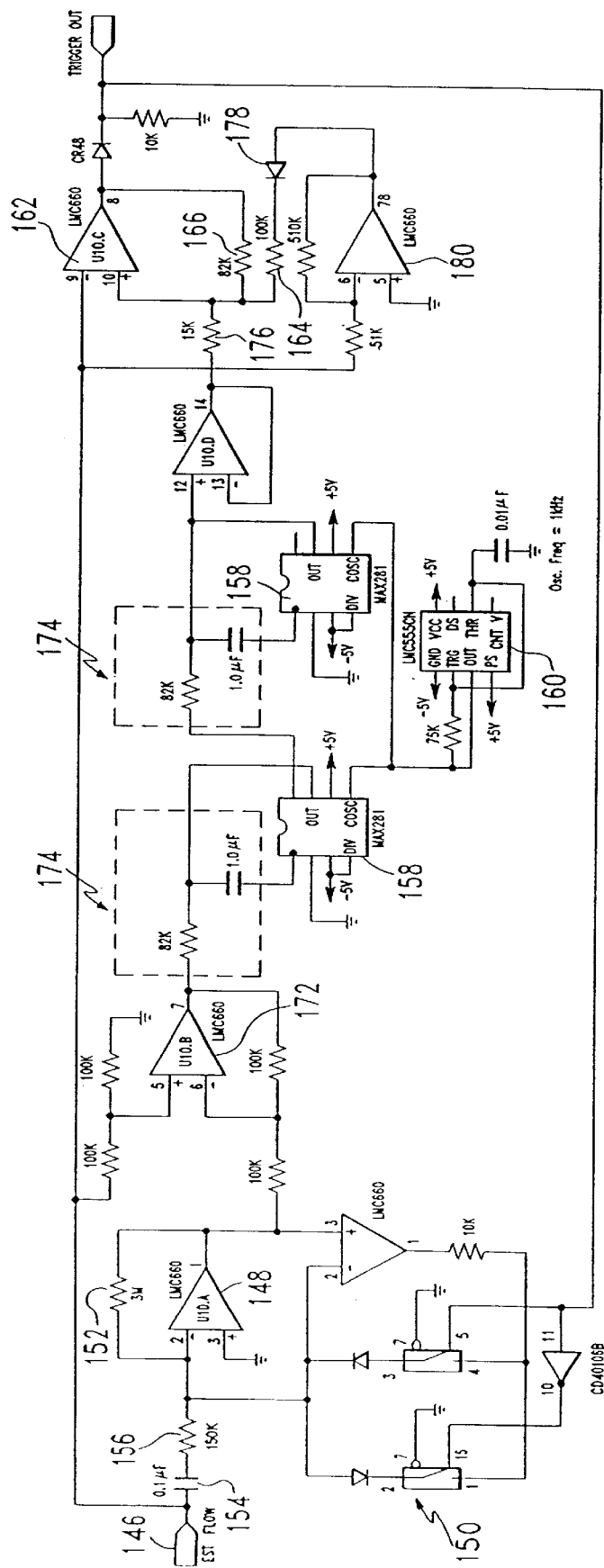
FIG. 8 is a schematic illustration of a circuit according to an embodiment of the invention.

A schematic diagram of one analog circuit embodying elements of the above-described improved trigger system is shown in FIG. 8. Input signal 146 is estimated patient flow, although it may alternatively be total flow. Use of estimated flow, in accordance with other aspects of the invention as described hereinabove, allows for further improved triggering if the system includes an unknown leak component. The input signal 146 is differentiated by inverting differentiator 148. The diodes, switches and operational amplifier group indicated generally at 150 are included for practical considerations. They form a switchable polarity ideal diode that is used to clip the large positive derivative of the flow trace at the beginning of inspiration, and the large negative derivative at the beginning of expiration. These derivatives are usually large, especially when ventilator pressure changes occur. If the large derivatives are not clipped, they can interfere with trigger circuit operation in the early part of each respiratory phase.

The differentiated input signal is scaled by feedback resistor 152 and input capacitor 154. These have a time constant equal to 300 milliseconds which is a preferred delay time for the delay portion of the circuit. The series input resistor 156 limits high frequency noise which is outside the range of breathing frequencies of interest. The differentiated input signal is subtracted from the flow signal in a difference amplifier 172 since the derivative circuit output is inverted and a sum is needed.

The requisite delay is produced using two fifth order, switched capacitor Bessel low pass filters 158. The Bessel filter has a linear phase shift with frequency which has the effect of providing a time delay. Since the time delay depends on the order of the filter as well as the frequency response, two filter sections are needed to provide a high enough cutoff frequency with the 300 millisecond time delay. The 300 millisecond delay was determined experimentally. This value seems appropriate in that the time constants for respiratory muscle activity are on the order of 50 to 100 milliseconds. Thus, a delay longer than 50 to 100 milliseconds would be needed to intercept flow changes caused by changes in respiratory muscle activity.

A 555 type timer chip 160 is set up as a 1 kHz oscillator. Along with the RC combination 174 at the Filter input, element 160 controls the cutoff frequency of the switched capacitor filters 158. Finally, a comparator 162 with hysteresis, provided by input resistor 176 and feedback resistors 166 and 164, changes its state based on the difference between the input flow rate signal and the processed flowrate signal. There is a fixed hysteresis during the inspirator phase caused by resistor 166. The hysteresis characteristic of the described circuit provides the negative offset during inspiration and the positive offset during expiration mentioned above.

During the expiratory phase, the hysteresis is initially greater than that during inspiration and is based on the magnitude of the flow signal as set by the current through resistor 164 and diode 178. The inverting amplifier 180 has a gain of 10 so that it saturates when the flow signal is greater than 0.5 volts, which corresponds to a flow of 30 liters per minute. The hysteresis is therefore almost doubled during the initial part of the exhalation phase by virtue of the 100 k resistor 164 in parallel with the 82 k resistor 166, in contrast with the 82 k resistor 166 acting alone during inspiration. That is, during exhalation the output of invertor 180 is positive. Therefore, diode 178 is forward biased and supplies current through resistor 164 in addition to that supplied by resistor 176.

Once the flow signal drops below the 0.5 volt level, the hysteresis decreases linearly with flow rate to be the same as that during inspiration. This feature prevents premature triggering to inspiration while gradually increasing the sensitivity of the system toward the end of exhalation. The hysteresis is somewhat dependent on the flow signal since it is supplied through a resistor 164. With the components described (82 k feedback resistor 166, 1.5 k input resistor 156) and a +5 volt system power supply (not shown), the hysteresis is about 90 millivolts at zero flow. This corresponds with a trigger offset of 90 cc per second above the instantaneous flow signal.

Figure 9:
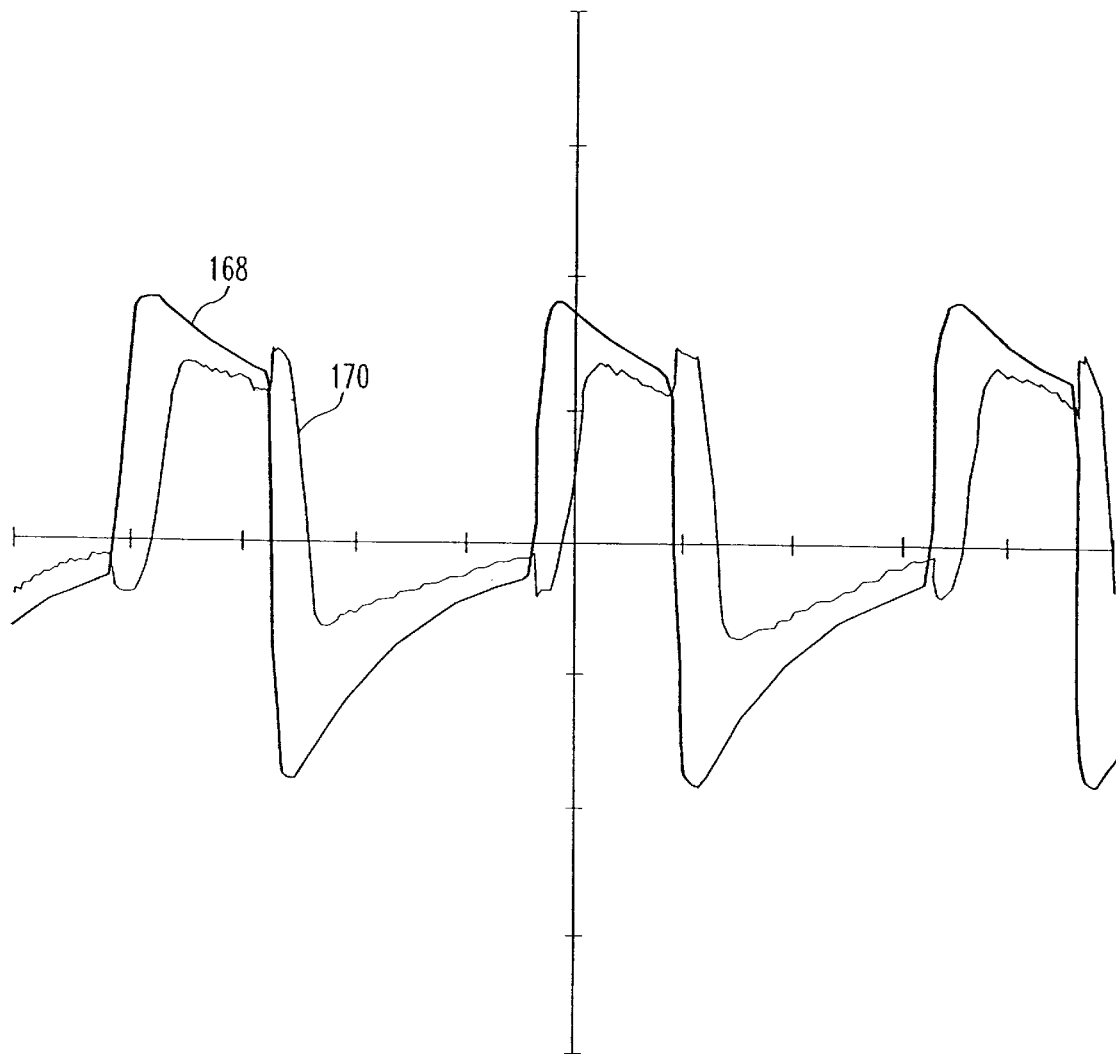
FIG. 9 is a trace of flow rate versus time showing processed and unprocessed flow rate signals.

FIG. 9 illustrates operation of the flow trace shape trigger circuit with the heavy line 168 indicating the flow signal at the − input and the lighter line 170 indicating the processed flow signal at the + input to the system comparator 162. Line 170 shows hysteresis decreasing as flow approaches zero during exhalation.

Figure 10A:
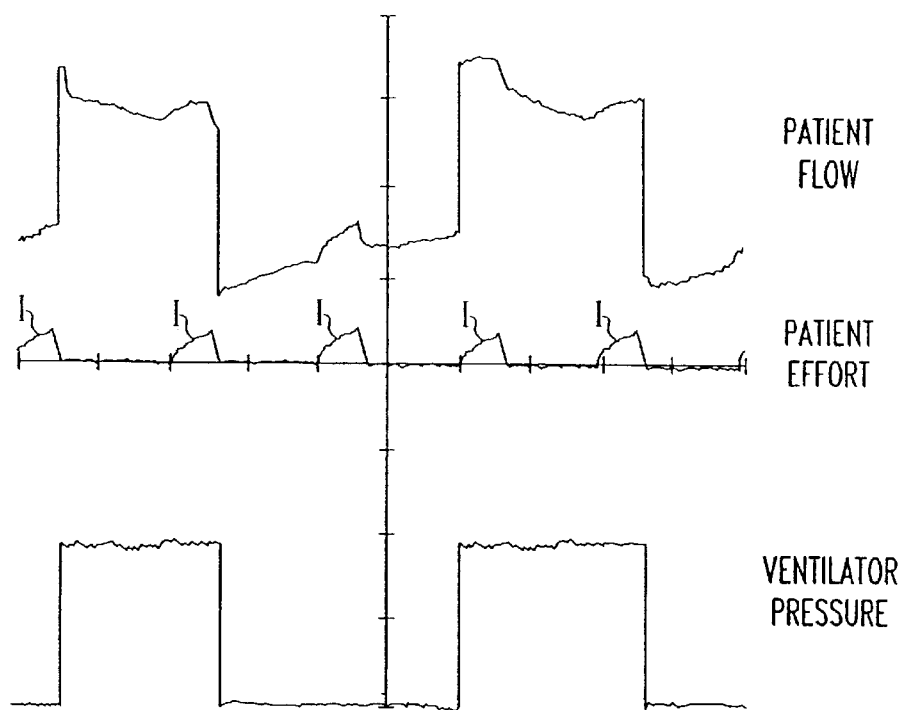
FIGS. 10a and 10b are illustrations of the operation of control algorithms according to other embodiments of the invention.
Figure 10B:
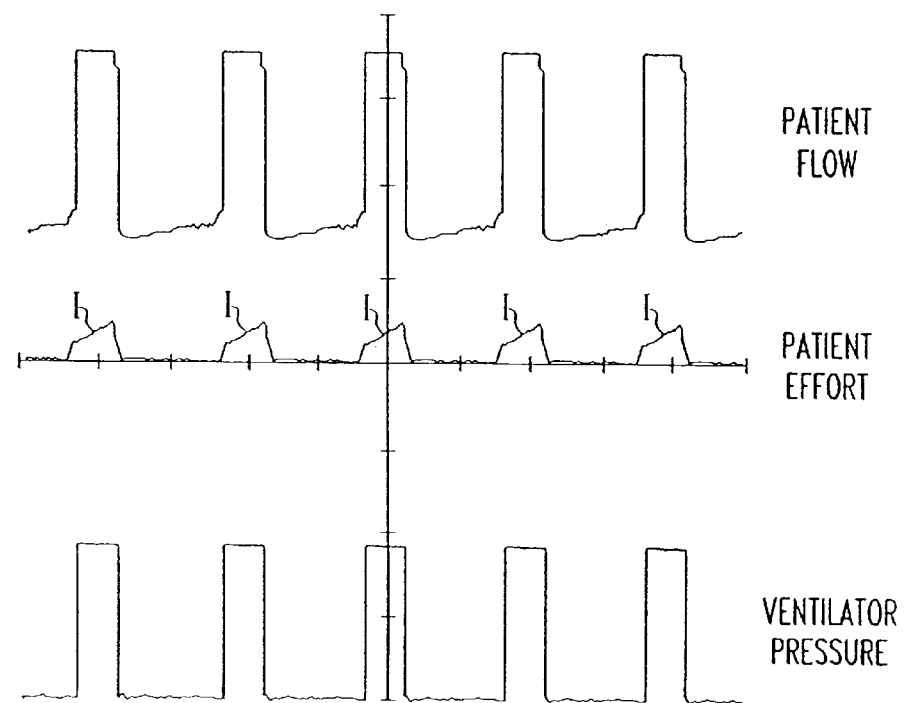

The triggering algorithm described immediately above is referred to as shape triggering (i.e. relying on changes in the shape or slope of the flow trace) to distinguish it from the flow triggering algorithm described earlier. FIGS. 10A and 10B illustrate the behavior of two ventilator triggering algorithms when used in a simulation of a spontaneously breathing patient with a large respiratory time constant. In each of FIGS. 10A and 10B, the uppermost trace represents estimated patient flow, the center trace represents patient respiratory effort, and the bottom trace represents ventilator pressure generated at the mask which interfaces with the patient airway. The letter I indicates patient inspiratory effort in each respiratory cycle.

As may be seen, FIG. 10A illustrates the sorts of triggering problems which were described hereinabove and which have been known to occur with actual patients. Patient inspiratory effort does not consistently trigger the ventilator, as shown by the asynchrony between patient effort, the estimated patient flow, and pressure generated at the mask. FIG. 10B, by contrast, illustrates ventilator response to the same simulated patient using the above-described shape triggering algorithm, but with all other settings unchanged. A comparison of FIG. 10A with 10B reveals the improved synchronization of delivered pressure with spontaneous patient effort.

It is noted that the simulated patient on which FIGS. 10A and 10B are based exhibits significant exhalatory flow at the beginning of an inspiratory effort. From FIG. 10B, it may be clearly seen that the shape triggering algorithm triggers appropriately at the beginning and end of each and every inspiratory effort even though the inspiratory effort begins while there is still exhalatory flow. Thus, the shapes triggering algorithm achieves the objective of synchronizing ventilator triggering with changes in patient effort.

Figure 11A:
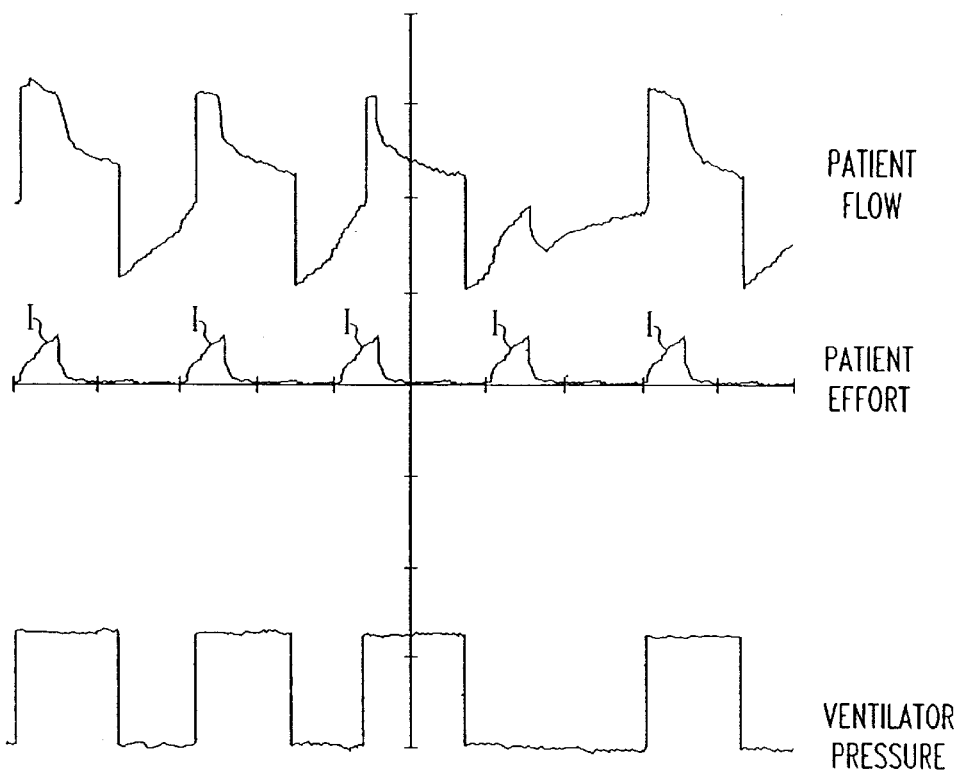
FIGS. 11a and 11b are illustrations of the operation of still other control algorithms according to other embodiments of the invention.
Figure 11B:
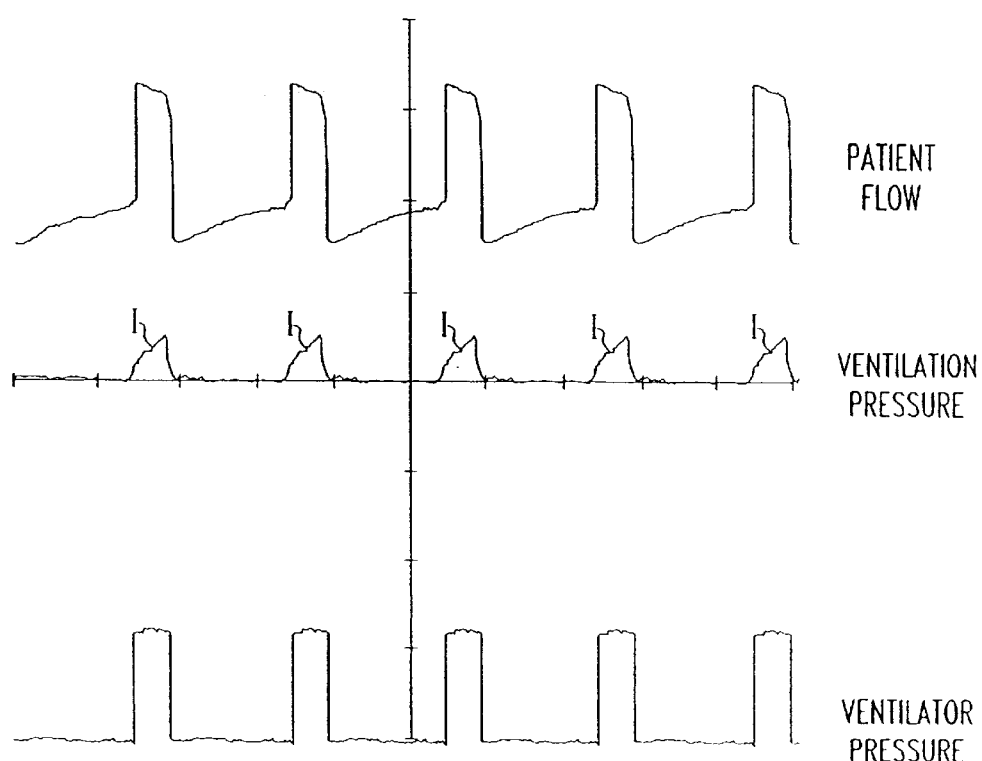

FIGS. 11A and 11B are similar to FIGS. 10A and 10B, respectively, but the simulated patient has a shorter respiratory system time constant. FIG. 11A illustrates, from top to bottom, estimated patient flow, patient respiratory effort, and pressure at the mask for a given triggering algorithm, and FIG. 11B illustrates the same parameters for the above-described flow trace shape triggering algorithm. In FIG. 11A it is clear that even with a substantial drop in flow when patient effort stops, the system does not trigger to EPAP until flow drops below about 25% of peak flow. Thus, the end of the inspiratory phase is not synchronized with the end of patient inspiratory effort. By contrast, the shape triggering algorithm of FIG. 11B produces, for the same patient, consistently synchronized triggering at the end of patient inspiratory effort.

As may be appreciated from the above description, a ventilator can be triggered on the basis of changes in the shape of the flow signal which correspond to changes in patient respiratory effort. This triggering algorithm solves several vexing problems which have limited the utility of some prior triggering algorithms such as standard pressure support triggering. It is also to be noted that the described flow signal shape triggering algorithm does not rely on any calculation of system leakage, although the shape triggering algorithm can operate more reliably with an estimate of system leakage than without it.

Although the described shape triggering algorithm works to trigger both to IPAP and to EPAP, it tends to work best for triggering to EPAP because normally a much larger and more abrupt change in patient respiratory effort occurs at the end of inspiration than at the beginning.

It will be noted further that the described shape triggering algorithm may be used in parallel with the earlier described flow triggering algorithm to provide a dual triggering system in which a secondary triggering algorithm will function in the event the primary algorithm malfunctions. This sort of dual triggering system can operate on a continuing breath-to-breath basis such that at any desired trigger point the secondary triggering algorithm will trigger the ventilator if the primary triggering algorithm does not.

Additional improvements in leak compensation techniques are also contemplated by this invention. As noted in the above description concerning leak compensation, the algorithm described there relies on two requirements as follows: (1) the patient's inhaled and exhaled volumes over time are the same, (and indeed if the patient's rest volume just prior to the beginning of inspiration is the same from breath to breath, the inhaled and exhaled volumes for each individual breath will also be the same); (2) when the patient is inhaling, total flow is greater than leak flow and when the patient is exhaling total flow is less than leak flow.

In the above description relating to leakage, only total patient circuit flow is actually measured even though this flow is made up of two components, patient flow and leakage flow. Further, in the above description concerning leakage the leak is not estimated as a function of pressure. Rather, an average leak is calculated by integrating total flow. Since patient inhalation volume and exhalation volume are essentially the same, the average flow over a complete respiratory cycle is generally equal to the average leak per cycle.

It is to be noted further that the leak component itself can have two components, namely the known or intended leak of an exhalation port and an unknown leak component resulting from one or more inadvertent leaks such as leakage across a mask seal or at a tubing connection. The unknown or inadvertent leak component would be quite difficult to determine exactly as it can be a function of both pressure and time. Therefore, to the extent it is necessary to determine this leak component, its value is estimated; however, significant leak management improvements can also be developed without separating the leak into its intended and inadvertent components.

Regardless of whether or not the overall leak can be characterized as a function of time or pressure, the objective is still to adjust the estimate of leakage so that its average value is the same as the average value of the true leak over integral respiratory cycles. Of course, the average of the true leak can be obtained as the average of total flow since the patient flow component of average total flow is zero.

If one assumes the leak is a function of pressure, such as the leak from a WHISPER SWIVEL™ connector, we then can assume the leak will likely be less at EPAP than it is at IPAP, with an average value corresponding to a pressure between EPAP and IPAP. That is, for a leak which is a function of pressure, the leakage rate at a lower pressure is less than the leakage rate at a higher pressure. This characteristic of leak flow can be utilized in algorithms other than that described hereinabove to compensate for system leakage.

In all systems described herein, the purpose of determining leakage is to thereby determine patient flow in an open system. Of course, a closed system ideally has no leaks, but in practice may have inadvertent leaks; however, in an open system gas flow from the system, whether by a regulated leak at an exhaust point or through inadvertent leaks from tubing connections and seal interfaces, will constitute a significant part of the total system flow. Accordingly, leakage in the patient circuit of an open system can be calculated by using the total flow as detected by a pneumotach. This parameter, which we refer to as raw flow, includes all flow leaving or entering the gas flow source (eg., a blower) via the patient circuit. Therefore, raw flow includes both patient flow and system leakage. The purpose of the described leak management algorithm is to separate raw flow into patient flow and leakage components.

It is not necessary to directly measure either the patient flow or leakage component of raw flow, but consequently the results of the leakage calculations are to be regarded as estimated values. One mode of leak management is discussed hereinabove with reference to FIGS. 1 to 5. The following algorithm description relates to alternative approaches to leak management.

For a non-pressure dependent leak, one first determines when patient inhalation begins. We refer to this point in the patient's respiratory cycle as a the breath trigger and use it as a reference point to compare patient inspiratory and expiratory volumes. By using the beginning of inspiration as a breath trigger point, the leakage calculation is done with the patient's beginning lung volume at approximately the same level for every calculation.

The breath trigger reference point is identified by satisfaction of two conditions as follows: (1) raw flow greater than average leak rate; and (2) patient is ready to inhale. Concerning the first of these conditions, the comparison of raw flow with average leak rate reveals whether the patient is inhaling or exhaling because, as noted above, the nature of the raw flow component is such that raw flow exceeds system leakage during patient inspiration and is less than system leakage during patient expiration.

The second condition, that of determining whether the patient its ready to inhale, is assessed by reference to either of two additional conditions as follows: (1) the patient has exhaled a predetermined fraction of the inhaled volume, for example ¼ of inhalation volume; or (2) the patient has exhaled for more than a predetermined time, for example 300 milliseconds. An alternative statement of the first of these conditions is that the patient's exhaled volume is at least a significant fraction of inspiratory volume. As to the second condition, an exhalation time of more than 300 milliseconds can be detected by comparison of raw flow with estimated average leakage rate since, as noted above, raw flow is less than estimated average leak rate during exhalation. If raw flow thus is less than the average leak rate for longer than 300 milliseconds, the condition is met. If either of the conditions 1 or 2 immediately above is met the patient is ready to inhale. Therefore, if either of the conditions is met and in addition the raw flow is greater than average leak rate, the conditions for a breath trigger are satisfied and the described conditions thus can be used to trigger the ventilator for an inspiratory cycle.

The seeming contradiction of requiring raw flow greater than average leak rate to satisfy one breath trigger condition, and raw flow less than average leak rate as one parameter that can satisfy the second breath trigger condition is explained as follows. The condition that raw flow is greater than average leak rate merely indicates that the patient has begun an inhalation cycle; that is, the patient has exerted the initial inspiratory effort that is revealed as raw flow exceeding average system leakage. However, as discussed hereinabove, since the raw flow signal can and does cross the average leak rate signal due to spurious noise in the raw flow signal, not all incidents of raw flow being greater than average leakage will denote the beginning of patient inspiratory effort. In fact, noise in the raw flow signal may typically result in multiple crossings between the raw flow signal and the average leak signal. Especially troublesome in this regard is noise causing a momentary − to + transition while the actual major condition is the flow crossing zero due to a true inspiratory to expiratory transition.

In order to avoid multiple triggers at these points of signal crossings that do not denote initial patient inspiratory effort, the additional ready-to-inhale condition is imposed. Under this condition, the raw flow greater than average leak condition is validated only if one of the two conditions indicating the patient's respiration was just previously in an exhalatory state is satisfied. In the case of the second of these conditions, the 300 millisecond duration of raw flow less than average leakage corresponds to patient exhalation. Thus, the time element plays a role in the described breath trigger algorithm and must be understood. Raw flow less than average leakage indicates exhalation which then provides a ready-to-inhale output. A subsequent reversal of raw flow to a value greater than average leakage indicates the detection of patient inspiratory effort. The breath trigger thus consistently initiates an inspiratory cycle in synchronism with spontaneous patient respiration.

When the breath trigger occurs, the ready-to-inhale parameter is reset to await satisfaction of one of the two conditions specified above that provides a ready-to-inhale validation. The breath triggering process is then repeated upon occurrence of the next patient inspiratory effort when raw flow again exceeds average system leakage.

The time interval between breath triggers from one breath to the next can be captured and the raw flow signal integrated over that time interval to find the raw volume or total volume for each breath. The raw volume may then be divided by the time between breath triggers, for example the time interval between the next successive pair of breath triggers, to determine a recent time rate of leakage.

It is noted that the patient's respiration from one breath trigger to the next, as represented by the integration of the raw flow signal, rises from zero volume to a maximum value comprised of inspiratory volume and leakage volume during inspiration. As the respiratory cycle continues through expiration, the continued integration of negative flow reduces the raw volume parameter progressively as the exhaled volume is subtracted. Thus, at the next breath trigger, the raw volume parameter from the prior breath is equal to only the leakage volume and any change in patient resting volume; however, this latter value generally is assumed to be zero.

Thus, as the raw volume parameter is really only leak volume, dividing that value by the time duration of the breath provides an estimate of the leak rate for the most recent breath. By averaging the recent leak rate over time an average leak rate can be determined to provide a more stable signal. Among other benefits, this reduces any effects of breath-to-breath volume variation resulting from breath-to-breath changes in patient resting volume. The number of respiratory cycles over which the recent leak may be averaged to determine average leak rate may be anywhere between one and infinity, depending upon the desired balance between signal stability and rapid error correction. Longer term averaging results in greater stability but slower error correction. Shorter term averaging provides less stability but quicker error correction.

Finally, it is to be noted that the average leak rate whose calculation is described here was used initially in this algorithm in one of the conditions for initiating a breath trigger. The parameters used in the conditions for initiating a breath trigger thus can be continually updated, used to satisfy the breath trigger conditions, and then the successive breath triggers are used in turn to again update these parameters.

A related approach to leakage analysis involves the use of a leak component which is, or is assumed to be, a function of patient circuit pressure. This sort of leak analysis can be useful in such ventilation regimens as, for example, proportional assist ventilation such as described in U.S. Pat. No. 5,107,830. It is important in proportional assist ventilation to know both the average leak rate and the instantaneous leak for the system. However, proportional assist ventilation involves variation of pressure according to the level of ventilation assistance required by the patient from moment to moment. Since at least some components of system leakage can be a function of pressure, those components will also vary more or less in synchronism with varying patient ventilation needs.

Thus, an alternative algorithm for leak analysis that can be used in a proportional assist ventilation system and in other systems as deemed suitable would be based on the requirement that patient flow equals raw flow, as defined hereinabove, less any known leak component and any pressure dependent leak component. Known leakage may be any leak, intentional or otherwise, having known flow characteristics, for example the leakage through a WHISPER SWIVEL™ or through a plateau exhalation valve. That is, the known leak is not necessarily a fixed leak, but can also be a function of pressure. Although such leaks of known characteristics could be lumped together with leaks having unknown characteristics but assumed to be functions of pressure, the following analysis can be carried out with leaks of known characteristics included or excluded from the leakage calculation described.

The pressure dependent leak, whether constituted of total leakage or only a component of total leakage, is calculated as a function of system pressure from analysis of the raw flow signal. One function by which the pressure dependent leak component is related to pressure is that for any orifice defining a pressure drop between a pressurized system and a lower pressure surrounding environment, the flow through the orifice will be proportional to the square root of the pressure difference across the orifice multiplied by a constant K, which characterizes the mechanical features of the orifice itself, that is its size, surface smoothness, and so forth.

To find the pressure dependent leak component, it is necessary only to characterize one hypothetical orifice as representing the source of all pressure dependent leakage. To find the hypothetical orifice, the breath trigger defined above is utilized to mark the beginning and end of patient respiratory cycles, and the average patient circuit pressure is measured for each breath. The average leak rate, as calculated hereinabove, is multiplied by the time duration of the previous breath to determine pressure dependent leak volume on a per-breath basis. If the pressure dependent leak component is separated from the known leak component, then the known leak component is also separated from average leak rate before the average leak rate is used to determine pressure dependent leak volume.

The pressure dependent leak volume is then divided by the average of the square root of pressure for the prior breath to give the corresponding orifice characteristic K. Over the next breath, the pressure dependent leak is found by multiplying the calculated orifice characteristic K by the square root of instantaneous pressure. This gives the pressure dependent leak rate as a function of pressure throughout the breath. This is an important parameter in such ventilation regimens as the above characterized proportional assist ventilation. More generally, however, it is important for the therapist to have reliable information on system leakage. The pressure dependent leak rate, therefore, can be useful for characterizing leakage in a variety of ventilation systems.

For either of the last described leak calculations, recovery routines are desired to deal with those instances when a breath trigger does not occur when it should due to failure of the raw flow signal to cross the average leak rate signal as the patient breaths. When the system leak changes, the raw flow signal will increase if the leak increases or decrease if the leak decreases. It is possible for this increase or decrease to be large enough that the raw flow signal never crosses the average leak rate, and when this occurs there will be no breath trigger and thus no new or updated leak calculations. To recover from such an incident, an algorithm is needed to begin the leakage calculations again and thereby bring the calculated average leak rate back into line with actual system functioning. Initiation of the recovery algorithm is determined to be necessary if any one of four known physiological events occurs as follows: (1) exhalation continues for more than 5 seconds; (2) inhalation continues for more than 5 seconds; (3) inspiratory tidal volume is greater than 5 liters; or (4) expiratory tidal volume is less than −1 liter.

The ventilator system should include elements for monitoring operation to detect occurrence of any one of these events. When one such event is detected, rediscovery of the leak is initiated by changing the average leak rate to the raw flow signal by gradually adding a percentage of the difference between raw flow and average leak to the average leak rate. Preferably, the percentage of difference added should be selected to provide a time constant of approximately one second.

As the gradual increase in average leak rate in accordance with the recovery algorithm causes the average leak rate value to approach raw flow value, the increasing average leak rate ultimately will cause a breath trigger in accordance with one of the triggering algorithms as described above, and the repetitive leak calculations will then resume with each respiratory cycle.

From the above leak management algorithm it may be seen that the algorithm may also be based on comparison of estimated patient flow to a zero value, and calculate only an unknown leak as a function of pressure. In a manner similar to the leak management algorithm above characterized, a breath indicator or trigger is employed as a marker for the start of patient inspiration. The breath trigger occurs when two conditions are met, namely: (1) estimated patient flow is greater than 0; and (2) patient is ready to inhale. The ready-to-inhale condition is satisfied when: (1) the patient has exhaled a specified portion (eg. 25%) of inspiratory volume; (2) estimated patient flow is less than 0; and (3) inspiratory volume is greater than a constant represented by 0 or a small positive value.

As with the above-described algorithms, the conditions requiring inspiratory volume to be both less than a percentage of expiratory volume and greater than a small positive value are not contradictory as these measurements are taken at different times. First, the ready-to-inhale condition must be satisfied by the specified parameters, including detection of an estimated patient flow less than zero since the last inhalation. Then, a breath trigger can occur when estimated patient flow goes positive since estimated patient flow greater than 0 indicates initial patient inhalatory effort.

From one breath trigger to the next, raw flow is integrated and the square root of pressure is also integrated. Then at the next breath trigger the unknown orifice is calculated by dividing the value obtained from raw flow integration by the value obtained from integration of the square root of pressure to provide the characteristic K for the unknown orifice. As noted above, the unknown orifice is a hypothetical leak source intended to describe the characteristic of leakage from all sources of pressure dependent leak.

Once the unknown orifice characteristic has been calculated, it is multiplied by the square root of patient circuit pressure at any time during the following breath to provide a measure of the instantaneous unknown leak. Estimated patient flow is then found by subtracting the instantaneous unknown leak from the raw flow.

In both of the algorithms which treat the system leak as the gas flowing through a hypothetical orifice of characteristic K, the constant K is calculated in essentially the same way. Although the equation for the calculation is derived differently for the two approaches, the result is the same, as follows.

$$K = \frac{\int_0^T (total\ flow)dt}{\int_0^T (\sqrt{Pressure})dt} \quad \text{eq. 1}$$

We have noted above that as one aspect of the invention, we calculate leakage as a function of gas pressure. Accordingly, the equation for calculating the constant K can be more generally stated as follows:

$$K = \frac{\int_0^T (total\ flow)dt}{\int_0^T f(P(t))dt} \quad \text{eq. 2}$$

In cases where the system also includes a known leak component such as a leak resulting from use of a plateau valve or a WHISPER SWIVEL™ as described above, the calculations can be modified to provide greater accuracy by subtracting the known leak component from raw flow prior to integration of raw flow to determine the unknown orifice, and also prior to utilizing raw flow to determine estimated patient flow. In this case, the integral of raw flow minus the known leak, divided by the integral of the square root of patient circuit pressure will provide the parameter K characterizing the unknown orifice attributable to only the unknown leak. That orifice characteristic K can then be multiplied by the square root of patient circuit pressure during the subsequent breath to provide a measure of the unknown leak component. Estimated patient flow at any time then would be found by subtracting both the known leak and the calculated unknown leak from the raw flow signal.

The modified algorithm preferably also includes a recovery routine for essentially the same reasons as earlier stated. A breath trigger for this modified algorithm depends upon estimated patient flow crossing the zero value as the patient breaths. When the leak value changes, both raw flow and estimated patient flow will increase if the leak is increasing, or decrease if the leak is decreasing. It is possible for such an increase or decrease to be large enough that estimated patient flow will never cross the 0 value. When this occurs no breath trigger occurs and there will be no new or updated leak calculations unless a recovery routine is performed.

To correct this condition, a recovery algorithm may be utilized to detect when leakage calculation is out of control according to two limiting parameters as follows: (1) inspiratory tidal volume is greater than a physiological value such as 4.5 liters; or (2) inspiratory tidal volume is less than a non-physiological value such as −1 liter. When either of these non-physiological events occurs, the leakage calculation is out of control and the system leak must be rediscovered by artificially inducing a breath trigger. Thus, the system would require flow detecting apparatus to sense the specified limiting values of inspiratory tidal volume and provide a breath trigger reference point. This restarts system operation essentially in the same manner as described above with reference to other algorithms, and thus initiates a new leak calculation. The data used for these continued calculations can include data from after the change in leak magnitude so that the estimate of the unknown leak is improved. Even if the new unknown leak value is incorrect, continuing repeated calculations also will be based on data from after the change in leak magnitude. Thus, the calculated estimate of unknown leak will continue to quickly approach reliable values.

Figure 12:
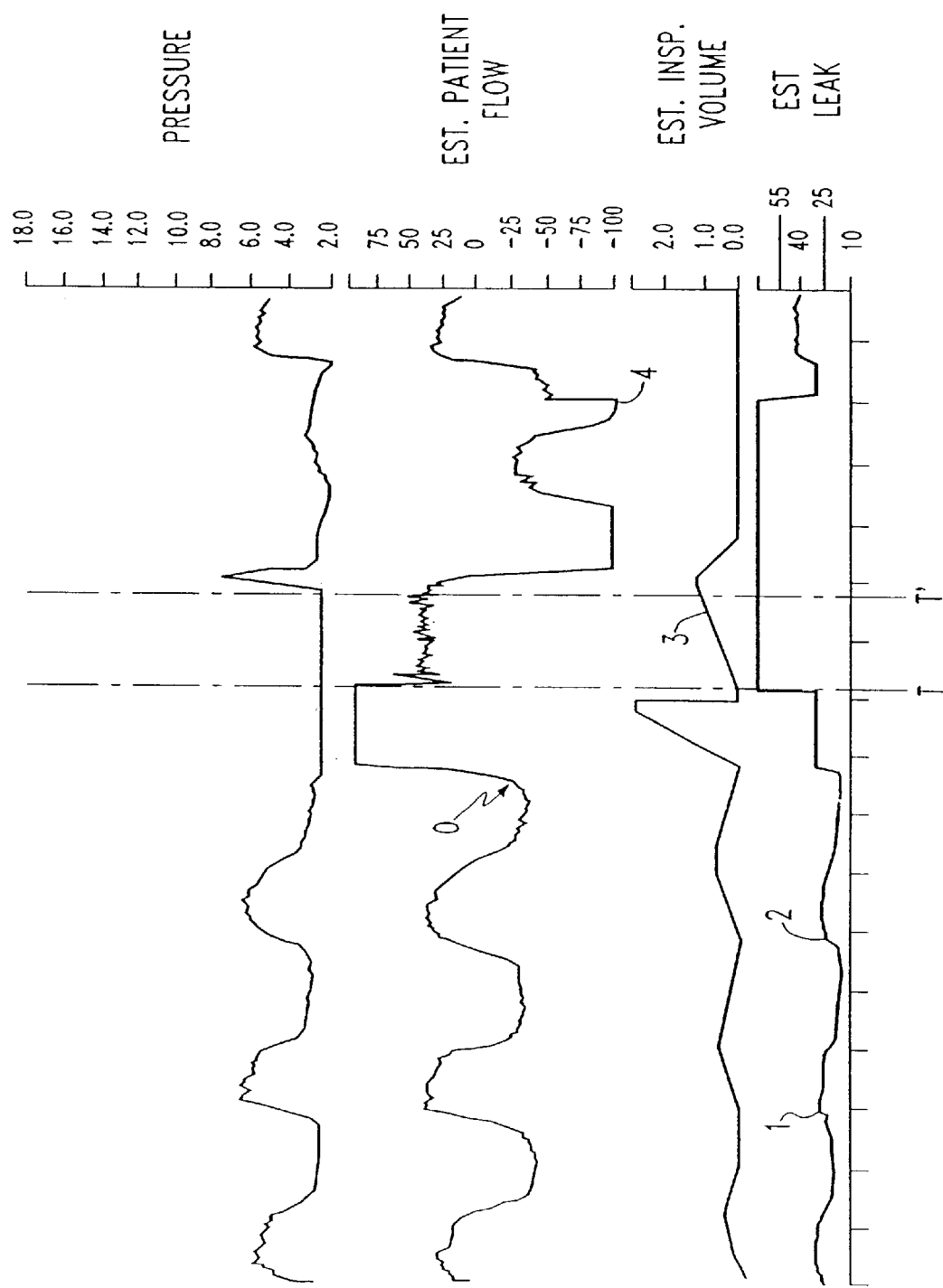
FIG. 12 illustrates operation of yet another control algorithm according to the invention.

FIG. 12 illustrates the described leak management algorithm in action, with intentional introduction of a very large leak. In FIG. 12, the four traces represent, from top to bottom, pressure, estimated patient flow, estimated inspiratory volume, and estimated leak (combined known and unknown leakage). The X axis is progressing time, moving from left to right.

As can be seen from FIG. 12, for the first three respiratory cycles the algorithm is able to determine leakage as a function of pressure. At the start of each inspiration an unknown orifice characteristic K is calculated. Points 1 and 2 on the estimated leak trace show the transitions between one unknown orifice characteristic K and the next, which is an updated unknown orifice characteristic. Point 2 on the estimated leak trace shows a much smoother transition between old and new unknown orifice characteristics than does point 1, thus indicating that point 2 is a transition between unknown orifice characteristics of essentially the same value.

To test algorithm response to leakage, a very large leak was introduced as indicated at point O on the estimated patient flow trace. Predictably, the estimated patient flow and estimated inspiratory volume rise off scale very quickly. At time T, estimated inspiratory volume has reached 4.5 liters and a breath trigger thus is forced. The resulting calculation estimates the leak to be a very high value which, in the estimated leak portion of FIG. 12 is off scale. The resulting estimated patient flow is approximately 50 liters per minute where in fact it should be zero. Tidal volume continues to rise rapidly as indicated at point 3 and would ultimately force another breath trigger when it reached the 4.5 liter limit. The large system leak is removed at time T', however, so the rise in tidal volume ceases.

With the leak removed from the system, estimated patient flow and estimated inspiratory volume rapidly drop off scale. Thus, when inspiratory tidal volume reaches the recovery limit of −1 liter, another breath trigger is forced thus leading to a new leak calculation and a resulting estimated leak lower than the previous leak calculation. This brings estimated patient flow back onto scale. Although the new leak calculation is better than the previous one, it is not by any means perfect. With estimated patient flow based on this new unknown leak orifice characteristic, tidal volume may once again drop below the −1 liter limit such as indicated at point 4 thus forcing another breath trigger. Once again a new unknown orifice calculation is performed and used for an unknown leak calculation which results in a very good value, thus returning the system to normal ranges of operation. The system thus was reliable in recovery from even very large changes in leak magnitude. The much smaller changes in leak magnitude that are more commonly encountered are readily handled under this algorithm by either the normal calculation or the recovery calculation.

Of course, we have contemplated various alternative and modified embodiments of the invention of which the above described are exemplary as the presently contemplated best modes for carrying out the invention. Such alternative embodiments would also surely occur to others skilled in the art, once apprised of our invention. Accordingly, it is intended that the invention be construed broadly and limited only by the scope of the claims appended hereto.

We claim:

1. A method of detecting changes in a respiratory state of a patient between inspiration and expiration, comprising:

monitoring a respiratory gas flow of such a patient;

determining, from the monitoring step, a respiratory gas flow characteristic at selected time intervals;

comparing selected pairs of said respiratory gas flow characteristics, wherein each selected pair of respiratory gas flow characteristics includes a predicted value of such a patient's respiratory gas flow rate at a selected time, and such a patient's actual respiratory gas flow rate at the selected time; and identifying, from the comparing step, changes in the patient's respiratory state between inspiration and expiration.

2. The method of claim 1, further comprising:

taking a derivative of a known patient respiratory gas flow rate; and processing the derivative to determine the predicted value of such a patient's respiratory gas flow rate.

3. The method of claim 2, wherein the processing step includes scaling the derivative with a scaling factor to obtain a scaled derivative.

4. The method of claim 3, wherein the processing step includes modifying the scaled derivative with an offset factor to determine the predicted value of such a patient's respiratory gas flow rate.

5. The method of claim 3, wherein the scaling factor includes a time factor.

6. The method of claim 5, the time factor is determined, at least in part, by a time span between the selected time and a time prior to the selected time.

7. The method of claim 1, wherein the predicted value of such a patient's respiratory gas flow rate is determined from an actual patient respiratory flow rate that occurred at a time prior to the selected time.

8. A method of determining a leak component of gas flow in a respiratory gas supply system for supplying respiratory gas to a patient, comprising:

determining a beginning and an end of an integral number of patient breaths;

integrating a patient respiratory gas flow rate throughout at least one breath to determine a total respiratory gas volume for the at least one breath; and dividing the total respiratory gas volume for the at least one breath by a time duration of the at least one breath to determine a leakage rate for the at least one patient breath.

9. The method of claim 8, further comprising averaging the leakage rate for the at least one patient breath to determine an average respiratory gas leakage from such a respiratory gas supply system.

* * * * *